United States Patent
Cutshall et al.

(10) Patent No.: US 6,777,432 B1
(45) Date of Patent: Aug. 17, 2004

(54) PHARMACEUTICAL USES AND SYNTHESIS OF NICOTINAMIDES

(75) Inventors: Neil S. Cutshall, Everett, WA (US); Scott C. Jeffrey, Everett, WA (US)

(73) Assignee: Darwin Molecular Corporation, Bothell, WA (US)

(*) Notice: Subject to any disclaimer, the term of this patent is extended or adjusted under 35 U.S.C. 154(b) by 116 days.

(21) Appl. No.: 10/237,258

(22) Filed: Sep. 4, 2002

Related U.S. Application Data

(60) Provisional application No. 60/317,281, filed on Sep. 4, 2001.

(51) Int. Cl.[7] .................. A61K 31/44; C07D 213/28
(52) U.S. Cl. .................. 514/345; 514/349; 546/290; 546/297
(58) Field of Search ................ 546/290, 297; 514/345, 349

(56) References Cited

FOREIGN PATENT DOCUMENTS

WO    WO-02060896    *    8/2002

OTHER PUBLICATIONS

Fleming, S. A., "Chemical Reagents in Photoaffinity Labeling", *Tetrahedron* (1995), vol. 51, pp 12479–12520.

Frevert, C. W., "Rapid Fluorescence–based Measurement of Neutrophil Migration in vitro", *Journal of Immunological Methods* (1998), vol. 213, pp 41–52.

Karlsson, R. et al., "Biosensor Analysis of Drug–Target Interactions: Direct and Competitive Binding Assays for Investigation of Interactions Between Thrombin and Thrombin Inhibitors", *Analytical Biochemistry* (Feb. 2000), vol. 278, pp 1–13.

Rosania, G. R., "Myoseverin, A Microtubule–binding Molecule with Novel Cellular Effects", *Nature Biotechnology* (Mar. 2000), vol. 18, pp 304–308.

Shimizu, N. et al., "High–performance Affinity Beads for Identifying Drug Receptors", *Nature Biotechnology* (Aug. 2000), vol. 18, pp 877–881.

* cited by examiner

Primary Examiner—Alan L. Rotman
Assistant Examiner—Janet L Coppins
(74) Attorney, Agent, or Firm—Seed IP Law Group PLLC

(57) ABSTRACT

A compound of the formula

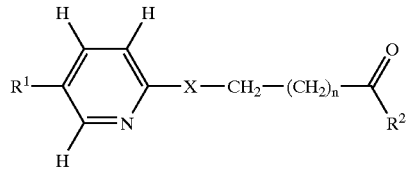

and pharmaceutically acceptable salts thereof, wherein $R^1$ is selected from $(R_3)C(=O)-N(R^4)-$ and $(R^3)(R^4)N-C(=O)-$; $R^2$ is selected from $-OR^5$ and $-N(R^5)(R^6)$; n is 0, 1, 2 or 3; X is selected from oxygen and sulfur; and $R^3$, $R^4$, $R^5$ and $R^6$ are independently selected from hydrogen, alkyl, heteroalkyl, aryl, aryl(akylene), heteroaryl, heteroaryl (alkylene), carbocycle, carbocycle(alkylene), heterocycle, and heterocycle(alkylene); as well as pharmaceutical compositions containing said compound. The compounds and compositions are useful in, for example, the treatment of inflammatory events in an animal subject.

50 Claims, No Drawings

PHARMACEUTICAL USES AND SYNTHESIS OF NICOTINAMIDES

CROSS-REFERENCE TO RELATED APPLICATION

This application claims the benefit of U.S. Provisional Patent Application No. 60/317,281 filed Sep. 4, 2001, where this provisional application is incorporated herein by reference in its entirety.

BACKGROUND OF THE INVENTION

1. Field of the Invention

The present invention relates to nicotinanilide compounds useful as pharmaceutical agents, to methods for their production, to pharmaceutical compositions which include these compounds, and to methods for their use in various therapies.

2. Description of the Related Art

Chemotactic cytokines (chemokines) are a class of potent inflammatory mediators that have the potential to attract specific subsets of leukocytes to sites of inflammation. Chemokines are typically low-molecular-mass (7–9 kd) proteins that can be divided into four subfamilies (CCC or β-subfamily, CXC or α-subfamily, $CX_3C$) and are categorized by their primary amino acid structure. The CXC subfamily is characterized by the two conserved Cys residues (C) near the N-terminus and separated by an amino acid (X). Some of the CXC chemokines, of which IL-8 and GRO-α are representative, belong further to the ELR+ subfamily (Glu-Leu-Arg) and are important in the recruitment and activation of neutrophils via the CXCR1 and CXCR2 receptors.

The interaction of chemokines with specific cell populations is mediated by G-protein-coupled seven-transmembrane receptors (7TMR). Chemokine receptors can be classified into four groups (CR, CCR, CXCR, CX3CR) based upon their primary amino acid sequence. The CXCR1 receptor binds with high affinity to IL-8 and low affinity to NAP-2, ENA-78 (epithelial cell-derived neutrophil-activating factor), GRO-α, -β, and -γ, whereas, CXCR2 binds with high affinity to all of the mentioned CXC chemokines. Both CXCR1 and CXCR2 receptors are found primarily on neutrophils and a subset of T-cells. W. Holmes et al., Science 253:1278 (1991); P. Murphy et al., Science 253:1280 (1991); A. Chuntharapai et al., J. Immunol. 153:5682 (1994); L. Xu et al., J. Leukocyte Biol. 57:335 (1995).

CXCR1 and CXCR2 have been shown to mediate the responses to CXC chemokines in neutrophils (polymorphonuclear neutrophils; PMN) and are essential to the acute inflammatory response. P. Grob et al., J. Biol. Chem. 265:8311 (1990); J. Besemer et al., J. Biol. Chem. 264:17, 409 (1989); A. Samanta et al., J. Exp. Med. 169:1185 (1989); W. Holmes et al., Science 253:1280 (1991); P. Murphy et al., Science 253:1280 (1991). Although both receptors are involved in neutrophil chemotaxis, in vitro studies using human neutrophils have inconclusively shown if chemotaxis is mediated by one or both receptors. IL-8 induced chemotaxis studies using anti-receptor monoclonal antibodies in CXCR1 and CXCR2 cell lines have led to conflicting reports. J. Quan et al., Biochem. Biophys. Res. Commun. 219:405 (1996); A. Chuntharapai et al., J. Immunol. 155:2587 (1995); M. Hammond et al., J. Immunol. 155:1428 (1995). There is also evidence to indicate that the transendothelial migration of CLA+ T-cells is a CXCR2 mediated event. L. Santamaria-Babi et al., Eur. J. Immunol. 26:2056 (1996).

The role, in inflammatory disorders, of neutrophil chemotaxis mediated by the CXCR1 and CXCR2 receptors is generally accepted. It has been reported that neutrophils are implicated in the pathogenesis of the acute respiratory distress syndrome (ARDS) in patients with sepsis. J. Repine et al., Am. Rev. Respir. Dis. 144:251 (1991). A causal role of PMNs in the lung injury associated with trauma is also widely accepted. G. Goldman et al., Ann. Surg. 212:513 (1990); S. Linas et al., Am. J. Physiol. 255:F728 (1988); R Simpson et al., Prog. Clin. Biol. Res. 388:265 (1994); S. Donnelly, Arch. Emerg. Med. 10:108 (1993); S. Donnelly, Resuscitation 28:87 (1994). For example, sepsis-related ARDS patients have increased levels of IL-8, ENA-78, ad GRO-α in their bronchoalveolar lavage fluids. R. Goodman et al., Am. J. Respir. Crit. Care Med. 154:602 (1996); J. Villard, Am. J. Respir. Crt. Care Med. 152:1549 (1995). Additionally, it has been demonstrated that CXCR1 functions as the single dominant CXC chemokine receptor for neutrophil chemotaxis in patients with sepsis. C. Cummings, J. Immunol. 162:2341 (1999).

High levels of IL-8 and tissue neutrophil infiltration have been observed in the synovial tissues of rheumatoid arthritis patients (H. Endo, Lymphokine Cytokine Res. 10:245 (1991)). Evidence has been presented that GRO-α and IL-8 are important mediators involved in the recruitment of neutrophils in the early and late phases of lipopolysaccharide-induced (LPS) rabbit arthritis. A. Matsukawa et al., Lab. Invest. 79:591 (1999). The murine CXCR2 receptor has also been shown to be necessary for neutrophilic inflammation in a mouse model of gouty synovitis. R. Terkeltaub et al., Arthritis. Rheum. 41:900 (1998).

CXC chemokines have attracted attention as being important in the development of atherosclerosis. R. Terkeltaub et al., Curr. Opin. Lipidol. 9:397 (1998). The role of CXCR1 and CXCR2 ligands on monocyte function in atherosclerosis in rabbits was published by D. Schwartz et al., J. Clin. Invest. 94:1968 (1994). Knockout mice that lacked CXCR2 expression had diminished lesion size. W. Boisvert et al., J. Clin. Invest. 101:353 (1998).

The involvement of the CXCR2 receptor in the pathological inflammatory response elicited by central nervous system (CNS) cells as related to Alzheimer's disease is also gaining significant attention. M. Xia et al., J. Neurovirol. 5:32 (1999). Reports have focused on the upregulation of CXCR2 expression on dystrophic neurites of senile plaques. M Xia et al., Am. J. Pathol. 150:1267 (1997); R. Horuk et al., J. Immunol. 158:2882 (1997).

High levels of IL-8 and neutrophil infiltration have been observed in the pathogenesis of a number of other disease indications.

This includes ulcerative colitis (Y. Mahida, Clin. Sci. 82:273 (1992); R. Izzo, Am J. Gastroenterol 87:1447 (1992)) and psoriasis (R. Gillitzer et al., J. Invest. Dermatol. 107:778 (1996); T. Kojima, J. Invest. Dermatol. 101:767 (1993)). CXCR1 and CXCR2 chemokines and their roles in tumor growth and metastasis have been reviewed. J. Wang, J. Immunol. Meth. 220:1 (1998).

To date, a limited number of CXCR1 and CXCR2 antagonists have been reported.

It was reported that a bis-aryl urea was able to selectively inhibit CXCR2 and prevent neutrophil migration and chemotaxis in a rabbit model. J. White, J. Biol. Chem. 273:10095 (1998). Other CXCR1 and CXCR2 receptor antagonists have focused on $NH_2$-terminal truncations and modifications of IL-8, GRO-α, and ELR motifs. S. Jones et al., *J. Biol. Chem.* 272:16166. Murine neutrophil recruitment in vivo could also be inhibited via CXCR2 receptor blocking using a truncated human GRO-α analog. There are currently no CXCR1 or CXCR2 receptor antagonist based therapies widely available.

There is a continued need for inhibitors of chemokine-mediated cellular events, such as those giving rise to an inflammatory response. Small molecule antagonists of CXC receptors and their ligands such as GRO-α and IL-8 would be useful in the control of harmful inflammatory processes as well as important tools for the investigation of receptor-ligand interactions.

BRIEF SUMMARY OF THE INVENTION

The present invention relates to novel nicotinamide compounds useful as pharmaceutical agents, to methods for their production, to pharmaceutical compositions that include these compounds and a pharmaceutical carrier, excipient or diluent, and to pharmaceutical methods of treatment. The compounds of the present invention may be administered to a subject in order to inhibit a chemokine-mediated cellular event. For example, the compounds may inhibit either of IL-8 or GRO-α driven chemotaxis. In particular, the compounds of the invention are useful for the prophylaxis and/or treatment of diseases or conditions involving inflammation due to neutrophil chemotaxis, i.e., the compounds of the invention may be used to inhibit neutrophil chemotaxis. The present invention also relates to intermediates and processes useful in the preparation of the nicotinamide compounds.

The nicotinamide compounds of the invention may achieve this biological efficacy themselves, or metabolites of the nicotinamide compounds may be primarily responsible for the biological effects observed upon administration of a nicotinamide compound of the invention to a patient. Thus, the nicotinamide compounds of the invention may have biological activity, and/or may function as prodrugs so that one or more metabolites of the nicotinamide compounds has the desired biological activity. formula (I)

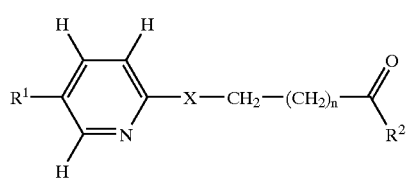

(I)

and pharmaceutically acceptable salts thereof. In compounds of the invention, $R^1$ is selected from

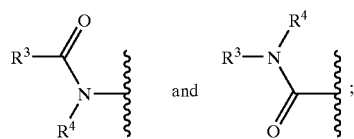

$R^2$ is selected from

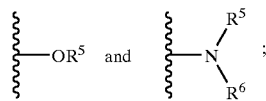

n is 0, 1, 2 or 3;
X is selected from oxygen and sulfur; and
$R^3$, $R^4$, $R^5$ and $R^6$ are each independently selected from hydrogen, alkyl, heteroalkyl, aryl, aryl(akylene), heteroaryl, heteroaryl(alkylene), carbocycle, carbocycle(alkylene), heterocycle, and heterocycle(alkylene).

In another aspect, the present invention provides composition comprising a compound or compounds of the present invention as set forth herein, and a pharmaceutically acceptable carrier, adjuvant or excipient.

In another aspect, the present invention provide a method for treating an inflammatory event. The method includes administering to a subject in need thereof a therapeutically effective amount of a nicotinamide compound of the present invention. In another aspect, the method includes administering to a subject in need thereof an amount of a nicotinamide compound of the invention, where the amount is effective to inhibit neutrophil chemotaxis.

In another aspect, the present invention provides a method for antagonizing a chemokine receptor in a subject. The method includes administering to a subject in need of thereof, an amount of a nicotinamide compound of the invention where the amount is effective to antagonize a chemokine receptor in the subject.

In another aspect, the present invention provides a method for inhibiting a chemokine-mediated cellular event. The method includes administering to a subject in need thereof an amount of a nicotinamide compound of the invention, where the amount is effective to at least partially inhibit a chemokine-mediated cellular event. The effective amount may be sufficient to inhibit a CXCR1 receptor in the subject. The effective amount may be sufficient to inhibit a CXCR2 receptor in the subject. The chemokine-mediate cellular event may be an IL-8 mediated cellular event. The chemokine-mediated cellular event may be a GRO-α mediated cellular event. The chemokine-mediated cellular event may be a granulocyte chemotactic protein 2 (GCP-2) mediated cellular event. The chemokine-mediated cellular event may be an epithelial cell-derived neutrophil attractant 78 (ENA-78) mediated cellular event. The chemokine-mediated cellular event may be a melanocyte growth stimulatory activity (MGSA) mediated cellular event. The chemokine-mediated cellular event may be a lipopolysacchaaride-induced CXC chemokine (L1X) mediated cellular event. The chemokine-mediated cellular event may be a GRO-β mediated cellular event. The chemokine-mediated cellular event may be a GRO-γ mediated cellular event. The chemokine-mediated cellular event may be a neutrophil-activating peptide-2 (NAP-2) mediated cellular event. The chemokine-mediate cellular event may be two or more of an IL-8 mediated cellular event, a GRO-α mediated cellular event, a granulocyte chemotactic protein 2 (GCP-2) mediated cellular event, an epithelial cell-derived neutrophil attractant 78 (ENA-78) mediated cellular event, a melanocyte growth stimulatory activity (MGSA) mediated cellular event, a lipopolysacchaaride-induced CXC chemokine (L1X) mediated cellular event, a GRO-β mediated cellular event, a GRO-γ mediated cellular event, and/or a neutrophil-activating peptide-2 (NAP-2) mediated cellular event. GRO- α, granulocyte chemotactic protein 2 (GCP-2), epithelial cell-derived neutrophil attractant 78 (ENA-78), melanocyte growth stimulatory activity (MGSA), lipopolysacchaaride-induced CXC chemokine (L1X), GRO-β, GRO-γ, and neutrophil-activating peptide-2 (NAP-2) are exemplary mediated cellular events.

In another aspect, the present invention provides a method for treating a disorder selected from psoriasis, atopic dermatitis, arthritis, asthma, chronic obstructive pulmonary disease, adult respiratory distress syndrome, inflammatory bowel disease, Crohn's disease, ulcerative colitis, stroke, septic shock, endotoxic shock, gram negative sepsis, toxic shock syndrome, cardiac and renal reperfusion injury, glomerulonephritis, thrombosis, graft vs. host reaction, Alzheimer's disease, allograft rejections, malaria, restinosis, angiogenesis and undesired hematopoietic stem cells release. The method includes administering to a subject in need thereof, an amount of a nicotinamide compound of the present invention, where the amount is sufficient to treat one or more of the disorders.

In another aspect, the present invention provides a method for inhibiting IL-8 or GRO-α driven chemotaxis in a subject. The method includes administering to a subject in need thereof, through a therapeutically acceptable manner, a therapeutically effective amount of a nicotinamide compound of the invention.

In these methods, the administration may be, for example, transdermal, oral, intravenous, intramuscular, vaginal, rectal, pulmonary, subcutaneous, sublingual and transmucosal administration.

The present invention also provides for identifying a binding partner to a nicotinamide compound of the present invention. In one method, a plurality of proteins known to be involved in the signaling pathway of chemotaxis are immobilized onto a suitable carrier; then a solution of one or more nicotinamide compounds, in isolation or mixture, as contacted with said proteins; then the presence of compound-:protein complex formation is analyzed using surface plasmon resonance (SPR). The signaling pathway of chemotaxis may be an IL-8 or GRO-α driven event. In another method, the present invention provides for identifying a binding partner to a nicotinamide compound of the present invention where the method includes providing said compound(s) bound to a solid support to provide solid phase compounds; contacting a cell or cell components with said solid phase compounds in isolation or mixture; removing uncomplexed cellular material; and recovering said binding partner from the solid phase compounds. Another method for identifying a binding partner to a nicotinamide compound as disclosed herein comprises: contacting a cell or cell components with nicotinamide compounds as described herein in isolation or in mixture, inducing a chemical reaction which will covalently link the compound to its binding partner, and then isolating and identifying the modified binding partner.

These and other related aspects of the present invention are set forth in more detail below.

DETAILED DESCRIPTION OF THE INVENTION

Definition of terms

"Alkyl" is a saturated or unsaturated, straight or branched, hydrocarbon chain. In various embodiments, the alkyl group has 1–18 carbon atoms, i.e., is a $C_1$–$C_{18}$ group, or is a $C_1$–$C_{12}$ group, a $C_1$–$C_6$ group, or a $C_1$–$C_4$ group. As referred to herein, a "lower alkyl" group has 1–6 carbons. Independently, in various embodiments, the alkyl group has zero branches (i.e., is a straight chain), one branch, two branches, or more than two branches. Independently, in one embodiment, the alkyl group is saturated. In another embodiment, the alkyl group is unsaturated. In various embodiments, the unsaturated alkyl may have one double bond, two double bonds, more than two double bonds, and/or one triple bond, two triple bonds, or more than two triple bonds. Exemplary alkyl groups include, without limitation, $CH_3$—, $CH_3CH_2$—, $CH_2$=$CH$—, $CH_3CH_2CH_2$—, $CH_2(CH_3)CH_2$—, $CH_3C(CH_3)_2CH_2$—. Alkyl chains may be substituted or unsubstituted. In one embodiment, the alkyl chains are unsubstituted. In another embodiment, the alkyl chain is substituted, e.g., with 1 substituent (i.e., the alkyl group is monosubstituted), or 1–2 substituents, or 1–3 substituents, or 1–4 substituents, etc. When substituted with a heteroatom, the substituted alkyl group may be referred to as a heteroalkyl.

"Alkylene" refers to a divalent alkyl radical, i.e., if hydrogen were to occupy one open valence site of an alkylene group then a alkyl group would result. Exemplary alkylene groups include, without limitation, —$CH_2$—, —$CH_2CH_2$—, —$CH$=$CH$—, —$CH_2CH_2CH_2$—, —$CH(CH_3)CH_2$—, —$CH_2C(CH_3)_2CH_2$—. As with alkyl groups, the alkylene group may be substituted or unsubstituted. In one embodiment, the alkylene group is unsubstituted. In another embodiment, the alkylene group is substituted, e.g., with 1 substituent (i.e., the alkylene group is monosubstituted), or 1–2 substituents, or 1–3 substituents, or 1–4 substituents, etc. When substituted with a heteroatom, the substituted alkylene group may optionally be referred to as a heteroalkylene. In one embodiment, the alkylene group is joined to an aryl group, so as to form an aryl(alkylene) group, also referred to as an aralkyl group. In one embodiment, aryl(alkylene) refers to $C_7$–$C_{20}$ groups, such as benzyl, α-methylbenzyl, α,α-dimethylbenzyl, phenylethyl (a.k.a. phenethyl), phenylpropyl, phenylbutyl and phenylhexyl are exemplary aralkyl groups. In another embodiment, the aralkyl group is $C_7$–$C_{11}$. In other embodiments, the alkylene group may be joined to a heteroaryl group (so as to form a heteroaryl(alkylene) group), a carbocycle group (so as to form a carbocycle(alkylene) group), and a heterocycle group (so as to form a heterocycle(alkylene) group).

"Aryl" is an aromatic hydrocarbon ring system. The ring system may be monocyclic or polycyclic (i.e., bicyclic, tricyclic, etc.). In various embodiments, the monocyclic aryl ring is $C_5$–$C_{10}$, or $C_5$–$C_7$, or $C_5$–$C_6$, where these carbon numbers refer to the number of carbon atoms that make up the ring system. A C6 ring system, i.e., phenyl, is a preferred aryl ring. In various embodiments, the polycyclic ring is a bicyclic aryl ring, where preferred bicyclic aryl rings are C8–C12, or C9–C10. A naphthyl ring, which has 10 carbon atoms, is a preferred polycyclic aryl ring. Aryl rings may be substituted or unsubstituted. In one embodiment, the aryl ring is unsubstituted. In another embodiment, the aryl ring is substituted with 1 substituent (i.e., the aryl ring is monosubstituted), or 1–2 substituents, or 1–3 substituents, or 1–4 substituents, etc.

"Carbocyclic aliphatic ring," also referred to as carbocycle or cycloalkyl, is a saturated or unsaturated, monocyclic or polycyclic (i.e., bicyclic, tricyclic, etc.) hydrocarbon ring. Carbocyclic aliphatic rings are not aromatic. A polycyclic hydrocarbon ring may include fused, spiro or bridged ring structures. In various embodiments, the monocyclic carbocyclic aliphatic ring is a C3–C10, or a C4–C7, or a C5–C6 ring system. In various embodiments, the polycyclic carbocyclic aliphatic ring is a C6–C12, or a C9–C10 ring system. In one embodiment, the polycyclic ring is bicyclic. In another embodiment, the polycyclic ring is bicyclic or tricyclic. Carbocyclic aliphatic rings include cyclopropylcyclopentyl, cyclohexyl, cyclohexenyl, cycloheptyl, and cyclooctyl. Carbocycles may be substituted or unsubstituted. In one embodiment, the carbocycle is unsubstituted. In another embodiment, the carbocycle is substituted with, e.g., 1 substituent (i.e., the alkyl group is monosubstituted), or 1–2 substituents, or 1–3 substituents, or 1–4 substituents, etc.

"Commercially available chemicals" may be obtained from standard commercial sources including Acros Organics (Pittsburgh, Pa.), Aldrich Chemical (Milwaukee, Wis., including Sigma Chemical and Fluka), Apin Chemicals Ltd. (Milton Park, U.K.), Avocado Research (Lancashire, U.K.), BDH Inc. (Toronto, Canada), Bionet (Cornwall, U.K.), Chemservice Inc. (West Chester, Pa.), Crescent Chemical Co. (Hauppauqe, N.Y.), Eastman Organic Chemicals, Eastman Kodak Company (Rochester, N.Y.), Fisher Scientific Co. (Pittsburgh, Pa.), Fisons Chemicals (Leicestershire, U.K.), Frontier Scientific (Logan, Utah), ICN Biomedicals, Inc. (Costa Mesa, Calif.), Key Organics (Cornwall, U.K.), Parish Chemical Co. (Orem, Utah), Pfaltz & Bauer, Inc. (Waterbury, Conn.), Polyorganix (Houston, Tex.), Pierce Chemical Co. (Rockford, Ill.), Riedel de Haen AG (Hannover, Germany), Spectrum Quality Product, Inc. (New Brunswick, N.J.), TCI America (Portland, Oreg.), Trans World Chemicals, Inc. (Rockville, Md.), and Wako Chemicals USA, Inc. (Richmond, Va.).

"Compounds described in the chemical literature" as referred to herein may be identified though various reference books and databases. Suitable reference books and treatise that detail the synthesis of reactants useful in the preparation of compounds of the present invention, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Quin, L. D. et al. "A Guide to Organophosphorus Chemistry" (2000), Wiley-Interscience, ISBN: 0-471-31824-8; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942–2000) John Wiley & Sons, in over 55 volumes; and "Chemistry of Functional Groups" John Wiley & Sons, in 73 volumes.

Specific and analogous reactants may also be identified through the indices of known chemicals prepared by the Chemical Abstract Service of the American Chemical Society, which are available in most public and university libraries, as well as through on-line databases (the American Chemical Society, Washington, D.C., www.acs.org may be contacted for more details). Chemicals that are known but not commercially available in catalogs may be prepared by custom chemical synthesis houses, where many of the standard chemical supply houses (e.g., those listed above) provide custom synthesis services.

"Haloalkyl" is an alkyl chain substituted with one or more halogens. A preferred haloalkyl is trifluoromethyl.

"Halogen" refers to fluoride, chloride, bromide or iodide. In a preferred embodiment, halogen refers to fluoride or chloride.

"Heteroalkyl" is a monovalent, saturated or unsaturated, straight or branched, chain containing carbon and at least one heteroatom. The heteroalkyl group may, in various embodiments, have one heteroatom, or 1–2 heteroatoms, or 1–3 heteroatoms, or 1–4 heteroatoms. Heteroalkyl chains may contain from 1 to 18 (i.e., 1–18) member atoms (carbon and heteroatoms) in the chain, and in various embodiments contain 1–12, or 1–6, or 1–4 member atoms. Independently, in various embodiments, the heteroalkyl group has zero branches (i.e., is a straight chain), one branch, two branches, or more than two branches. Independently, in one embodiment, the heteroalkyl group is saturated. In another embodiment, the heteroalkyl group is unsaturated. In various embodiments, the unsaturated heteroalkyl may have one double bond, two double bonds, more than two double bonds, and/or one triple bond, two triple bonds, or more than two triple bonds. Heteroalkyl chains may be substituted or unsubstituted. In one embodiment, the heteroalkyl chain is unsubstituted. In another embodiment, the heteroalkyl chain is substituted. A substituted heteroalkyl chain may have 1 substituent (i.e., be monosubstituted), or may have 1–2 substituents, or 1–3 substituents, or 1–4 substituents, etc.

"Heteroalkylene"-refers to an alkylene group wherein one or more of the carbons is replaced with a heteroatom.

Thus, the heteroalkylene group is a saturated or unsaturated, straight or branched chain divalent radical that contains at least one heteroatom. The heteroalkylene group may, in various embodiments, have one heteroatom, or 1–2 heteroatoms, or 1–3 heteroatoms, or 1–4 heteroatoms. Heteroalkylene chains may contain from 1 to 18 (i.e., 1–18) member atoms (carbons and/or heteroatoms) in the chain, and in various embodiments contain 1–12, or 1–6, or 1–4 member atoms. Independently, in various embodiments, the heteroalkylene group has zero branches (i.e., is a straight chain), one branch, two branches, or more than two branches. Independently, in one embodiment, the heteroalkylene group is saturated. In another embodiment, the heteroalkylene group is unsaturated. In various embodiments, the unsaturated heteroalkylene may have one double bond, two double bonds, more than two double bonds, and/or one triple bond, two triple bonds, or more than two triple bonds.

"Heteroaryl" is an aromatic ring system containing carbon and at least one heteroatom, that is, the heteroaryl group includes at least one aromatic ring containing a heteroatom, i.e., a heteroaryl ring. The heteroaryl ring may, in various embodiments, have 1 heteroatom, 1–2 heteroatoms, 1–3 heteroatoms, or 1–4 heteroatoms in the heteroaryl ring.

Heteroaryl groups may be monocyclic or polycyclic (i.e. bicyclic, tricyclic, etc.), where the polycyclic ring may contain fused, spiro or bridged ring junctions. In one embodiment, the heteroaryl is monocyclic, while in another embodiment the heteroaryl group is selected from monocyclic and bicyclic rings. Monocyclic heteroaryl rings may contain from about 5 to about 10 member atoms (carbon and heteroatoms), preferably from 5–7, and most preferably from 5–6 member atoms in the ring. Bicyclic heteroaryl groups may contain from about 8–12 member atoms, or 9–10 member atoms in the rings. In a polycyclic heteroaryl group, at least one ring contains heteroatoms, and the heteroatom-containing ring is aromatic. The additional rings may or may not, independently in each ring, contain heteroatom(s). If an additional ring contains heteroatom(s), then in various embodiments an additional ring has 1 heteroatom, 1–2 heteroatoms, or 1–3 heteroatoms. Independently, the additional rings may or may not be aromatic, that is, they may be saturated, unsaturated but not aromatic, or aromatic. The heteroaryl group may be unsubstituted or substituted. In one embodiment, the heteroaryl group is unsubstituted. In another embodiment, the heteroaryl group is substituted. The substituted heteroaryl group may, in various embodiments, contain 1 substituent, 1–2 substituents, 1–3 substituents, or 1–4 substituents. Exemplary heteroaryl groups include, without limitation, benzofuran, benzothiophene, furan, imidazole, indole, isothiazole, oxazole, pyrazine, pyrazole, pyridazine, pyridine, pyrimidine, pyrrole, quinoline, thiazole and thiophene.

"Heteroatom" is a nitrogen, sulfur, or oxygen atom. Groups containing more than one heteroatom may contain different heteroatoms, i.e., heteroatoms are selected on an independent basis upon each occurrence.

"Heterocyclic aliphatic ring," also referred to as heterocyclyl or cycloheteroalkyl or heterocycloalkyl, is a saturated or unsaturated, monocyclic or polycyclic (i.e., bicyclic, tricyclic, etc.) ring containing carbon and at least one heteroatom. Heterocyclic aliphatic rings are not aromatic. The heterocyclic aliphatic ring may, in various embodiments, have one heteroatom, or 1–2 heteroatoms, or 1–3 heteroatoms, or 1–4 heteroatoms, etc. In one embodiment, the heterocyclic aliphatic ring is monocyclic, where the monocyclic ring may have 3–10, or 4–7, or 5–6 member atoms. In another embodiment, the heterocyclic aliphatic ring is polycyclic, where in various embodiments, the ring may be bicyclic, or may be tricyclic, or may be either bicyclic or tricyclic. A polycyclic ring system may have one or more fused, spiro or bridged ring systems. The polycyclic heterocyclic aliphatic ring system may have 6–12, or 9–10 member atoms. The heterocyclic ring may be unsubstituted or substituted. In one embodiment, the heterocyclic ring is unsubstituted. In another embodiment, the heterocyclic ring is substituted. The substituted heterocyclic ring may contain 1 substituent, or 1–2 substituents, or 1–3 substituents, or 1–4 substituents, etc. Exemplary heterocyclic aliphatic rings include piperazyl, morpholinyl, tetrahydrofuranyl, tetrahydropyranyl and piperidyl.

"Lower alkyl" is an alkyl chain comprised of 1–6, preferably 1–4 carbon atoms.

"Pharmaceutically acceptable salt" and "salts thereof" means organic or inorganic salts of the pharmaceutically important molecule. A pharmaceutically acceptable salt may involve the inclusion of another molecule such as an acetate ion, a succinate ion or other counterion. The counterion may be any organic or inorganic moiety that stabilizes the charge on the parent compound. Furthermore, a pharmaceutically important organic molecule may have more than one charged atom in its structure. Situations where multiple charged atoms are part of the molecule may have multiple counterions.

Hence, the molecule of a pharmaceutically acceptable salt may contain one or more than one charged atoms and may also contain one or more than one counterion. The desired charge distribution is determined according to methods of drug administration. Examples of pharmaceutically acceptable salts are well known in the art but, without limiting the scope of the present invention, exemplary presentations can be found in the Physician's Desk Reference, The Merck Index, The Pharmacopoeia and Goodman & Gilman's The Pharmacological Basis of Therapeutics.

"Phenyl" refers to a six-membered aromatic carbocyclic ring of the structure

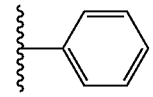

and, unless substitutents are specifically identified, the phenyl may be substituted with, in various aspects, 1, or 2, or 3, or 4, or, if no substitution and/or amount thereof is specifically defined, 5 substituents. In addition to the various substituents defined below, the substituent on the phenyl may be selected from a group of substituents defined by one or more, in any combination, of the following features: is an electron withdrawing group; an electron donating group; is hydrophobic; is hydrophilic; is organic; is inorganic; has 1–20 carbons; has 1–15 carbons; has 1–10 carbons; has 1–6 carbons; has 1–20 atoms; has 1–15 atoms; has 1–10 atoms; has 1–6 atoms; is an alkyl; is a heteroalkyl; is an aryl; is an aralkyl; and/or is a heteroaryl, including groups of one or more thereof in any combination. In one aspect the substituent is selected from groups of substituents containing one or more of the following substituents in any combination: azide, halogen, nitro, cyano, $C_{1-6}$alkyl, $C_{1-6}$haloalkyl, hydroxy, mercaptan, $C_{1-6}$alkoxy, carboxylic acid, carboxylate salt, and carboxylate ester. For example, the substituent may be selected from azide, fluoride, iodide (two specific halogens), hydroxyl and methyl (one specific alkyl having 1–6 carbons).

The present invention includes within its scope prodrugs of the compounds of this invention. In general, such prodrugs will be functional derivatives of the compounds of this invention which are readily convertible in vivo into the indicated compound. Conventional procedures for the selection and preparation of suitable prodrug derivatives are described, for example, in "Design of Prodrugs," ed. H. Bundgaard, Elsevier, 1985. Metabolites of these compounds include active species produced upon introduction of compounds of this invention into the biological milieu.

"Substituents" replace a hydrogen atom with a non-hydrogen atom on an alkyl, heteroalkyl, aryl, heteroaryl, carbocycle, and/or heterocyclyl group as defined herein. Where the substituent contains a heteroatom, that heteroatom may be at any acceptable oxidation state for that particular atom, e.g., sulfur as part of a substituent may vary from an oxidation state of −2 to +8, and may be part of a complex or chelate as in a sulfoxide a mercapto-phosphine or metal chelated in a thia-crown ether. Suitable substituents that may be located on one or more of these groups include the following: alkoxy (i.e., alkyl—O—, e.g., methoxy, ethoxy, propoxy, butoxy, pentoxy), aryloxy (e.g., phenoxy, chlorophenoxy, tolyloxy, methoxyphenoxy, benzyloxy, alkyloxycarbonylphenoxy, alkyloxycarbonyloxy, acyloxyphenoxy), acyloxy (e.g., propionyloxy, benzoyloxy, acetoxy), carbamoyloxy, carboxy, mercapto, alkylthio, acylthio, arylthio (e.g., phenylthio, chlorophenylthio, alkylphenylthio, alkoxyphenylthio, benzylthio, alkyloxycarbonyl-phenylthio), amino (e.g., amino, mono- and di- C1–C3 alkanylamino, methylphenylamino, methylbenzylamino, C1–C3 alkanylamido, acylamino, carbamamido, ureido, guanidino, nitro and cyano). Moreover, any substituent may have from 1–5 further substituents attached thereto.

"Amino" means a trivalent amine substituted with up to 2 alkyl groups as defined above or with 1 alkyl group and a hydrogen group, or with one aryl and one alkyl groups, or with two aryl groups, or with two or more hydrogen groups or with the substitution required to complete the nitrogen's valence requirements. "Amino" further includes amino salts where the nitrogen is hypervalent, having four bonds and may or may not have a charge and a counterion. The counterion, when present, may be an external inorganic and/or organic counterion and/or may be an internal counterion. Inorganic counterions include, for example, anions such as halo anions and other non-metal anions. Examples of organic counterions include, for example, anionic organic moieties such as acetate, citrate and other anionic organic moieties.

Compounds

In one aspect, the present invention provides compounds of the formula (I)

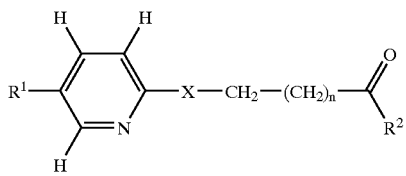

and pharmaceutically acceptable salts, solvates and prodrugs thereof. In compounds of the invention,

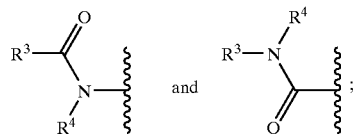

$R^1$ is selected from
$R^2$ is selected from

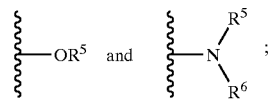

n is 0, 1, 2 or 3;
X is selected from oxygen and sulfur; and
$R^3$, $R^4$, $R^5$ and $R^6$ are each independently selected from hydrogen, alkyl, heteroalkyl, aryl, aryl(akylene), heteroaryl, heteroaryl(alkylene), carbocycle, carbocycle(alkylene), heterocycle, and heterocycle(alkylene).

Thus, the present invention provides nicotinamide compounds where an amide group is directly attached to the aromatic ring via either the nitrogen or the carbon atom of the amide functionality. In one embodiment of the invention, the amide group is attached to the aromatic ring via the amide's nitrogen atom, i.e., $R^1$ is $R^3$—C(=O)—N($R^4$)—. Thus, in one aspect, the present invention provides compounds of the formula

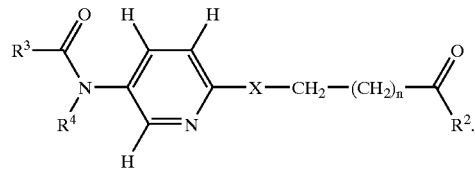

In another embodiment, the amide group is attached to the aromatic ring via the amide's carbonyl group, i.e., $R^1$ is $(R^3)(R^4)$N—C(=O)—. Thus, in another aspect, the present invention provides compounds of the formula

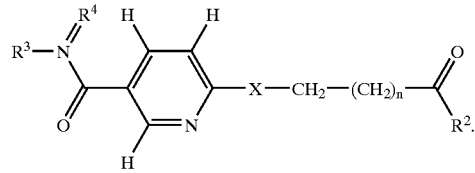

Also directly attached to the aromatic ring are three hydrogens and an X group. The X group is either an oxygen atom or a sulfur atom. Thus, in various embodiments of the invention, $R^1$ is $R^3$—C(=O)N($R^4$)— and either X is O, or X is S, or X is selected from S and O. The invention also provides compounds wherein $R^1$ is $(R^3)(R^4)$N—C(=O)— and either X is O, or X is S, or X is selected from S and O.

In compounds of the invention, $R^2$ is selected from —$OR^5$ and —N($R^5$)($R^6$). Thus, in one embodiment of the invention, $R^2$ is —$OR^5$, while in another embodiment $R^2$ is —N($R^5$)($R^6$), and in yet another embodiment $R^2$ may be either —$OR^5$ or —N($R^5$)($R^6$). In various embodiments, the present invention therefore provides compounds wherein $R^1$ is $R^3$—C(=O)—N($R^4$)—, X is O, and $R^2$ is —$OR^5$; $R^1$ is $R^3$—C(=O)—N($R^4$)—, X is S, and $R^2$ is —$OR^5$; $R^1$ is $R^3$—C(=O)—N($R^4$)—, X is selected from S and O, and $R^2$ is —$OR^5$; $R^1$ is $R^3$—C(=O)—N($R^4$)—, X is O, and $R^2$ is —N($R^5$)($R^6$); $R^1$ is $R^3$—C(=O)—N($R^4$)—, X is S, and $R^2$ is —N($R^5$)($R^6$); $R^1$ is $R^3$—C(=O)—N($R^4$)—, X is select from S and O, and $R^2$ is —N($R^5$)($R^6$); $R^1$ is $(R^3)(R^4)$N—C(=O)—, X is O, and $R^2$ is —$OR^5$; $R^1$ is $(R^3)(R^4)$N—C(=O)—, X is S, and $R^2$ is —$OR^5$; $R^1$ is $(R^3)(R^4)$N—C(=O)—, X is selected from S and O, and $R^2$ is —$OR^5$; $R^1$ is $(R^3)(R^4)$N—C(=O)—, X is O, and $R^2$ is —N($R^5$)($R^6$); $R^1$ is $(R^3)(R^4)$N—C(=O)—, X is S, and $R^2$ is —N($R^5$)($R^6$); $R^1$ is $(R^3)(R^4)$N—C(=O)—, X is selected from S and O, and $R^2$ is —N($R^5$)($R^6$).

In compounds of the invention, an alkylene chain is located between the X group directly attached to the aromatic ring, and a carbonyl group attached to $R^2$. In various embodiment of the invention, the alkylene group may consist of one methylene group (n=0), two methylene groups (n=1), three methylene groups (n=2), four methylene groups (n=3); one or two methylene groups (n=0,1); or two, three or four methylene groups (n=1,2,3). Each of these options for n may be combined with each of the various embodiments set forth above to provide unique aspects of the present invention.

For instance, in various aspects, the present invention provides compounds wherein $R^1$ is $R^3$—C(=O)—N($R^4$)—, X is O, $R^2$ is —$OR^5$, and n=0; $R^1$ is $R^3$—C(=O)—N($R^4$)—, X is S, $R^2$ is —$OR^5$, and n=0; $R^1$ is $R^3$—C(=O)—N($R^4$)—, X is selected from S and O, $R^2$ is —$OR^5$, and n=0; $R^1$ is $R^3$—C(=O)—N($R^4$)—, X is O, $R^2$ is —N($R^5$)($R^6$), and n=0; $R^1$ is $R^3$—C(=O)—N($R^4$)—, X is S, $R^2$ is —N($R^5$)($R^6$), and n=0; $R^1$ is $R^3$—C(=O)—N($R^4$)—, X is selected from S and O, $R^2$ is $-N(R^5)(R^6)$, and n=0; $R^1$ is $(R^3)(R^4)$N$-$C(=O)$-$, X is O, $R^2$ is $-OR^5$, and n=0; $R^1$ is $(R^3)(R^4)$N$-$C(=O)$-$, X is S, $R^2$ is $-OR^5$, and n=0; $R^1$ is $(R^3)(R^4)$N$-$C(=O)$-$, X is selected from S and O, $R^2$ is $-OR^5$, and n=0; $R^1$ is $(R^3)(R^4)$N$-$C(=O)$-$, X is O, $R^2$ is $-N(R^5)(R^6)$, and n=0; $R^1$ is $(R^3)(R^4)$N$-$C(=O)$-$, X is S, $R^2$ is $-N(R^5)(R^6)$, and n=0; $R^1$ is $(R^3)(R^4)$N$-$C(=O)$-$, X is selected from S and O, $R^2$ is $-N(R^5)(R^6)$, and n=0. The present invention also provides aspects wherein n=1 instead of n=0 in each of the previously listed aspects. The present invention also provides aspects wherein n=2 instead of n=0 in each of the previously listed aspects. The present invention also provides aspects wherein n=3 instead of n=0 in each of the previously listed aspects. The present invention also provides aspects wherein n=0 or 1 instead of requiring that n only be 0 in each of the previously listed aspects. The present invention also provides aspects wherein n=1, 2, or 3 instead of n=0 in each of the previously listed aspects.

Thus, when $R^2$ is $-OH$, the present invention provides compounds of the formula

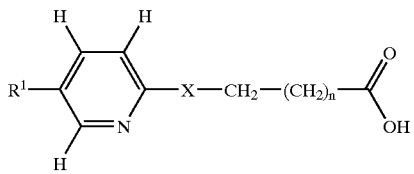

and prodrugs, solvates, and pharmaceutically acceptable salts thereof, wherein
$R^1$ is selected from

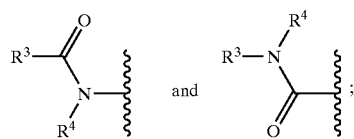

n is 0, 1, 2 or 3;
X is selected from oxygen and sulfur; and
$R^3$, $R^4$, $R^5$ and $R^6$ are independently selected from hydrogen, alkyl, heteroalkyl, aryl, aryl(akylene), heteroaryl, heteroaryl(alkylene), carbocycle, carbocycle(alkylene), heterocycle, and heterocycle (alkylene).

In each of the many foregoing aspects of the present invention, $R^3$, $R^4$, $R^5$ and $R^6$ are each independently selected from hydrogen, alkyl, heteroalkyl, aryl, aryl(akylene), heteroaryl, heteroaryl(alkylene), carbocycle, carbocycle (alkylene), heterocycle, and heterocycle(alkylene). However, in additional aspects of the invention, $R^3$, $R^4$, $R^5$ and/or $R^6$ is selected from more limited ranges of options. For example, in various aspects of the invention, each of $R^3$, $R^4$, $R^5$ and $R^6$ optionally and independently contains no more than 25, or 20, or 15, or 10 carbon atoms. In addition to the maximum number of carbon atoms in each of these groups, or independent of the total number of carbon atoms in a group, in various aspects of the invention each of $R^3$, $R^4$, $R^5$ and $R^6$ optionally and independently has a molecular weight of less than 500, or less than 400, or less than 300, or less than 200 g/mol. Overall, the compounds of the present invention preferably have a molecular weight of less than 5,000, or less than 4,000, or less than 3,000, or less than 2,000, or less than 1,000 g/mol according to various aspects of the invention, where each of these aspects may be independently combined with other aspects of the invention as previously set forth.

In one aspect of the invention, $R^3$ is hydrogen or lower alkyl; $R^4$ is aryl; and $R^5$ is selected from hydrogen and $C_1$–$C_{10}$alkyl, $C_1$–$C_{10}$heteroalkyl, $C_6$–$C_{12}$aryl, $C_6$–$C_{12}$aryl($C_1$–$C_6$akylene), $C_1$–$C_6$heteroaryl, $C_1$–$C_6$heteroaryl-($C_1$–$C_6$alkylene), $C_5$–$C_{10}$carbocycle, $C_5$–$C_{10}$carbocycle($C_1$–$C_6$alkylene), $C_1$–$C_6$heterocycle, and $C_1$–$C_6$heterocycle ($C_1$–$C_6$alkylene). Preferably, n=0 and/or $R^2$ is $-OR^5$. In a separate preferred embodiment, n=0 and $R^2$ is $-N(R^5)(R^6)$. Optionally, $R^5$ is selected from hydrogen and $C_1$–$C_{10}$alkyl, $C_6$–$C_{12}$aryl, $C_6$–$C_{12}$aryl($C_1$–$C_6$akylene), $C_5$–$C_{10}$carbocycle, and $C_5$–$C_{10}$carbocycle($C_1$–$C_6$alkylene. In another optional embodiment, $R^3$ is hydrogen and $R^4$ is phenyl substituted with one or more groups selected from fluorine, azide, hydoxyl, iodide and methyl. In a further optional embodiment, $R^3$ is hydrogen, $R^4$ is phenyl, and $R^5$ is hydrogen or alkyl. In a still further optional embodiment, $R^3$ is hydrogen, $R^4$ is phenyl, $R^5$ is alkyl, aryl or heteroaryl, and $R^6$ is hydrogen or alkyl.

Preparation of Compounds

Compounds of the present invention may be prepared from readily available starting materials according to methodology set forth in the synthetic schemes below. For instance, as illustrated in Scheme 1, either 6-hydroxynicotinic acid (Chemical Abstracts Registry No. 5006-66-6) or 6-mercaptonicotinic acid (Chemical Abstracts Registry No. 92823-43-3), (1) both of which are available from Aldrich (Milwaukee, Wis.; www.sigma-aldrich.com) may be coupled to a primary or secondary amine, $HNR^3R^4$ (2) to prepare the amide (3). Primary and secondary amines of the formula $HNR^3R^4$ where $R^3$ and $R^4$ are each independently selected from hydrogen, alkyl, heteroalkyl, aryl, aryl(akylene), heteroaryl, heteroaryl(alkylene), carbocycle, carbocycle(alkylene), heterocycle, and heterocycle (alkylene), are commercially available chemicals and/or are compounds described in the chemical literature.

Suitable conditions for this type of coupling involve performing the reaction in a suitable solvent, e.g., tetrahydrofuran (THF), in the presence of a suitable coupling agent, e.g., 2-ethoxy-1-ethoxycarbonyl-1,2-dihydroquinoline (EEDQ), and if necessary, a suitable tertiary amine such as diisopropylethylamine (DIEA).

Alkylation of X, the 6-mercapto or 6-hydroxy substituent, may be accomplished by treatment with the desired organo halide compound such as propyl bromoacetate, in an appropriate solvent such as N,N-dimethylformamide (DMF) or acetone, and an excess of an appropriate base such as sodium carbonate or cesium carbonate, to provide the corresponding product (4). Numerous organo halide compounds, i.e., compounds of the formula halide-$CH_2$—$(CH_2)$n—C(=O)—$R^2$, are commercially available chemicals and/or are compounds described in the chemical literature.

Scheme 1

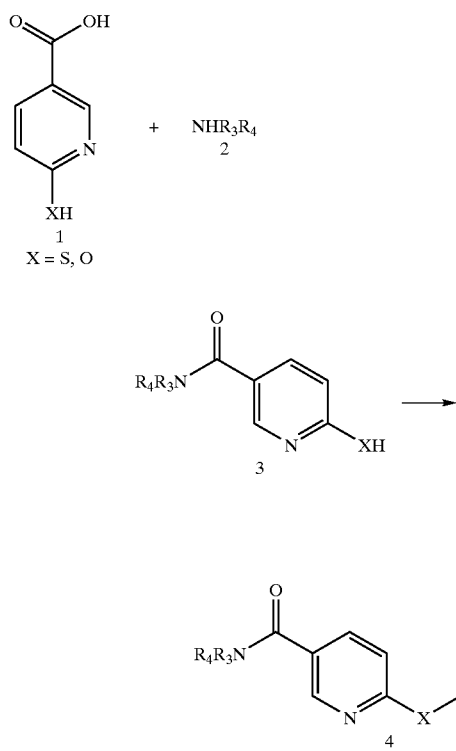

In an alternative route to preparing compounds of the present invention, 6-chloronicotinic acid (Chemical Abstracts Registry No. 5326-23-8) or 6-bromonicotinic acid (5a), or the corresponding acid chlorides (5b) may be coupled to a primary or secondary amine, $HNR^3R^4$ (2). In the case of using nicotinic acid, the corresponding anhydride, either mixed or symmetrical, may be employed as a reactant. If nicotinic acid is employed, then reaction with the amine may be carried out in the presence of a coupling agent such as carbodiimide reagent or EEDQ to form the amide (6). If the corresponding acid chloride compound (5b) is used, this may be treated with the appropriate amine, $HNR^3R^4$, in the presence of a base an appropriate solvent, such as dichloromethane, acetonitrile, DMF, THF and the like, at a temperature from 20° C. to 120° to form nicotinamides 6.

6-Chloro or 6-bromonicotinic acid analogs (6) may then be treated with the appropriate compound of the formula $HX-CH_2-(CH_2)_n-C(O)-R_{2a}$ in the optional presence of base such as potassium tert-butoxide, and in an appropriate solvent such as pyridine, ethylene glycol, DMF, DME, DMSO or the like, at a temperature from about 20° C. to 180° C. to form product (4a). Treatment of 4a with an excess of the appropriate alcohol ($R_{2b}$-H), either neat or in a solvent such as THF, toluene, benzene, or the like, in either a sealed or open tube under reflux conditions, at a temperature from about 20° C. to 180° C., and in the presence of a catalytic amount of acid such as sulfuric or hydrochloric acid could provide the transesterified product 4b. Treatment of 4a or 4b under aqueous basic conditions such as NaOH (aq) with or without a co-solvent such as THF, at a temperature from −20° C. to 180° C. followed by acidification with aqueous acid such as HCl (aq) provided acid 7. Acid 7 may be coupled to the appropriate amine via an anhydride, either mixed or symmetrical, or alternatively by treatment with the appropriate amine in the presence of a coupling agent such as carbodiimide reagent, PYBROP, or EEDQ to form the corresponding amide (8).

Scheme II

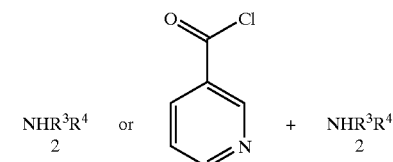

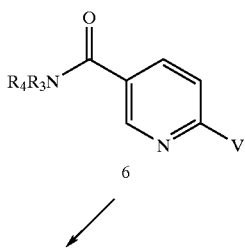

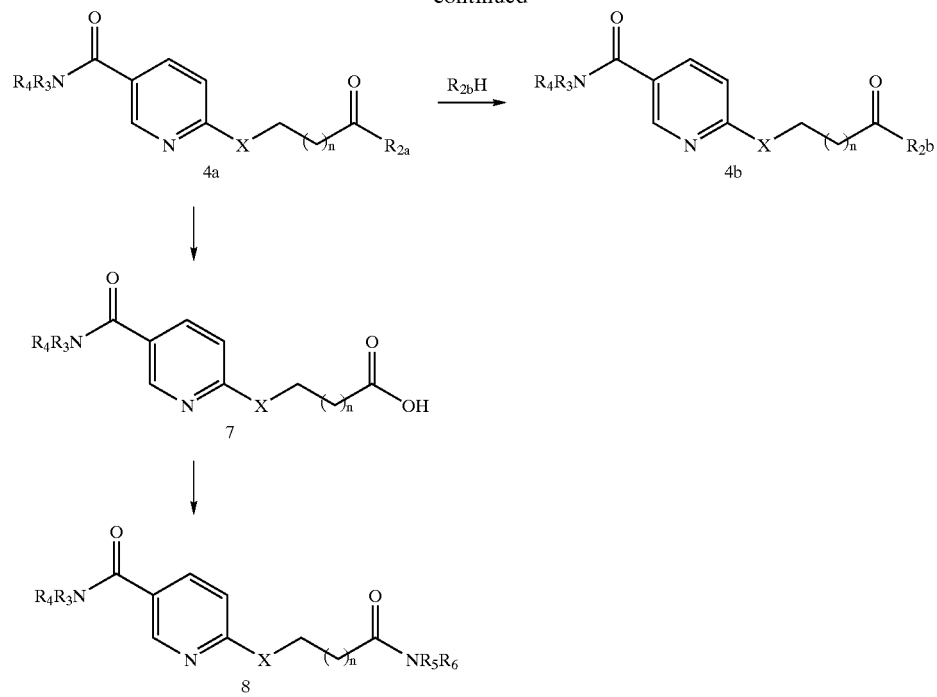

Yet another route to compounds of the present invention is illustrated in Scheme 3. 2-Halo-5-nitro-pyridine analogs (9) may be treated with a compound of the formula $HX-CH_2-(CH_2)n-C(O)-R_2$ where X is O or S, in the presence of base and in the appropriate solvent such as THF at a temperature from about 20° C. to 180° C. to form 2-substituted-5-nitropyridines (10). Reduction of the nitro group may be performed by treatment of 10 with hydrogen gas in the presence of palladium on carbon or Raney nickel, or alternatively, by treament with $SnCl_2$ in ethyl acetate or an alcoholic solvent and in the optional presence of HCl to obtain the corresponding 2-substituted-5-amino pyridines (11). Compound of formula 11 may be acylated with an appropriate acid halide (e.g., $RC(=O)Cl$ or $RC(=O)Br$) in the presence of a base such as pyridine, DMAP or the like, or alternatively may be acylated with an anhydride, either mixed or symmetrical, or alternatively may be acylated by treatment with the appropriate acid ($RCO_2H$) in the presence of a coupling agent such as a carbodiimide, PYBROP, or EEDQ, to form the final product (12).

Scheme III

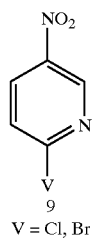

9
V = Cl, Br

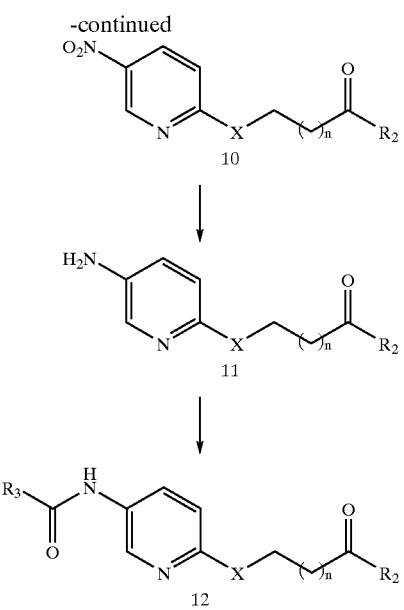

Pharmaceutical Compositions

In another aspect, the present invention provides a composition containing a nicotinamide compound of formula (I) in admixture with a pharmaceutically acceptable adjuvant, carrier, diluent or excipient, i.e., the present invention provides a pharmaceutical composition containing a compound of formula (I). The pharmaceutical composition may contain optional ingredient(s) if desired.

The pharmaceutical compositions of the present invention may be in any form which allows for the composition to be administered to a patient. Typical routes of administration include, without limitation, oral, topical, parenteral, sublingual, rectal, vaginal, and intranasal. The term parenteral as used herein includes subcutaneous injections, intravenous, intramuscular, intrasternal injection or infusion techniques. Pharmaceutical composition of the invention are formulated so as to allow the active ingredients contained therein to be bioavailable upon administration of the composition to a patient. Compositions that will be administered to a patient take the form of one or more dosage units, where for example, a tablet may be a single dosage unit, and a container of nicotinamide in aerosol form may hold a plurality of dosage units.

The composition may be in the form of a solid, liquid or gas (aerosol). In one aspect, the carrier(s) are particulate, so that the compositions are, for example, in tablet or powder form. The carrier(s) may be liquid, with the compositions being, for example, an oral syrup or injectable liquid. In addition, the carrier(s) may be gaseous, so as to provide an aerosol composition useful in, e.g., inhalatory administration.

When intended for oral administration, the composition is preferably in either solid or liquid form, where semi-solid, semi-liquid, suspension and gel forms are included within the forms considered herein as either solid or liquid.

As a solid composition for oral administration, the composition may be formulated into a powder, granule, compressed tablet, pill, capsule, chewing gum, wafer or the like form. Such a solid composition will typically contain one or more inert diluents or edible carriers. In addition, one or more of the following adjuvants may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin, a flavoring agent such as peppermint, methyl salicylate or orange flavoring, and a coloring agent.

When the composition is in the form of a capsule, e.g., a gelatin capsule, it may contain, in addition to materials of the above type, a liquid carrier such as polyethylene glycol or a fatty oil.

The composition may be in the form of a liquid, e.g., an elixir, syrup, solution, emulsion or suspension. The liquid may be for oral administration or for delivery by injection, as two examples. When intended for oral administration, preferred composition contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid pharmaceutical compositions of the invention, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or digylcerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid compositions intended for either parenteral or oral administration should contain an amount of the inventive compound such that a suitable dosage will be obtained. Typically, this amount is at least 0.01% of a compound of the invention in the composition. When intended for oral administration, this amount may be varied to be between 0.1 and about 70% of the weight of the composition. Preferred oral compositions contain between about 4% and about 50% of the active vanadium(V) complex. Preferred compositions and preparations according to the present invention are prepared so that a parenteral dosage unit contains between 0.01 to 1% by weight of active compound.

The pharmaceutical composition may be intended for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device. Topical formulations may contain a concentration of the inventive compound of from about 0.1 to about 10% w/v (weight per unit volume).

The composition may be intended for rectal administration, in the form, e.g., of a suppository which will melt in the rectum and release the drug. The composition for rectal administration may contain an oleaginous base as a suitable nonirritating excipient. Such bases include, without limitation, lanolin, cocoa butter and polyethylene glycol.

The composition may include various materials which modify the physical form of a solid or liquid dosage unit. For example, the composition may include materials that form a coating shell around the active ingredients. The materials which form the coating shell are typically inert, and may be selected from, for example, sugar, shellac, and other enteric coating agents. Alternatively, the active ingredients may be encased in a gelatin capsule.

The composition in solid or liquid form may include an agent which binds to the nicotinamide compounds of the invention and thereby assists in the delivery of the active compound. Suitable agents which may act in this capacity include a monoclonal or polyclonal antibody, a protein or a liposome.

Materials used in preparing the pharmaceutical compositions should be pharmaceutically pure and non-toxic in the amounts used. It will be evident to those of ordinary skill in the art that the optimal dosage of the active ingredient(s) in the pharmaceutical composition will depend on a variety of factors. Relevant factors include, without limitation, the type of subject (e.g., human), the particular form of the active ingredient, the manner of administration and the composition employed.

The pharmaceutical composition of the present invention may consist of gaseous dosage units, e.g., it may be in the form of an aerosol. The term aerosol is used to denote a variety of systems ranging from those of colloidal nature to systems consisting of pressurized packages. Delivery may be by a liquefied or compressed gas or by a suitable pump system which dispenses the active ingredients. Aerosols of compounds of the invention may be delivered in single phase, bi-phasic, or tri-phasic systems in order to deliver the active ingredient(s). Delivery of the aerosol includes the necessary container, activators, valves, subcontainers, and the like, which together may form a kit. Preferred aerosols may be determined by one skilled in the art, without undue experimentation.

Whether in solid, liquid or gaseous form, the pharmaceutical composition of the present invention may contain one or more known pharmacological agents used in the treatment of inflammation.

The pharmaceutical compositions may be prepared by methodology well known in the pharmaceutical art. For example, a composition intended to be administered by injection can be prepared by combining a nicotinamide compounds of formula (I) with water so as to form a solution. A surfactant may be added to facilitate the formation of a homogeneous solution or suspension. Surfactants are compounds that non-covalently interact with the nicotinamide compound so as to facilitate dissolution or homogeneous suspension of the compound in the aqueous delivery system.

Biological Applications

The present invention provides specific nicotinamides and compositions containing a nicotinanilide that may be used to inhibit a chemokine-mediated cellular event. The chemokine-mediated event may involve a CXC ligand that can function as a neutrophil activator and/or chemoattractant. These ligands include, without limitation: growth-related oncogene (GRO)-α, GRO-β, Gro-γ, neutrophil-activating peptide-2 (NAP-2), granulocyte chemotactic protein 2 (GCP-2); MGSA; and epithelial cell-derived neutrophil attractant 78 (ENA-78). The selectivity of the above ligands for their corresponding receptors is as follows: CXCR1: IL-8, GCP-2; and CXCR2: IL-8. MGSA (melanocyte growth stimulatory activity), GRO-α, GRO-β, GRO-γ, NAP-2, GCP-2, and ENA-78/LIX/CXCL5.

The epithelial neutrophil activating peptide 78 (ENA-78), also called lipopolysaccharide-induced CXC chemokine (LIX), has been recognized as a potent chemoattractant and activator of neutrophil functions. Also, ENA-78 is produced by many non-hematopoietic cell types. It has been observed that ENA-78 expression is elevated in the inflamed tissues of patients with rheumatoid arthritis, Crohn's disease, ulcerative colitis, acute appendicitis, allergic airway inflammation (Waltz at al, 1997). ENA-78 is also a potent angiogenic factor in small lung cancer. Accordingly, the compounds of the present invention may be used in methods whereby these receptors are antagonized.

Thus, in one aspect, the event involves IL-8, including IL-8a (CXCR1 receptor) and IL-8b (CXCR2 receptor). In another aspect the event involves GRO-α.

In another aspect, the present invention provides a method for treating an inflammatory event. The method includes administering to a subject in need thereof a therapeutically effective amount of a nicotinamide compound of the present invention. In another aspect, the method includes administering to a subject in need thereof an amount of a nicotinamide compound of the invention, where the amount is effective to inhibit neutrophil chemotaxis.

In another aspect, the present invention provides a method for antagonizing a chemokine receptor in a subject. The method includes administering to a subject in need thereof, an amount of a nicotinamide compound of the invention where the amount is effective to antagonize a chemokine receptor in the subject.

In another aspect, the present invention provides a method for inhibiting a chemokine-mediated cellular event. The method includes administering to a subject in need thereof an amount of a nicotinamide compound of the invention, where the amount is effective to at least partially inhibit a chemokine-mediated cellular event. The effective amount may be sufficient to inhibit a CXCR1 receptor in the subject. The effective amount may be sufficient to inhibit a CXCR2 receptor in the subject. The chemokine-mediate cellular event may be an IL-8 mediated cellular event. The chemokine-mediated cellular event may be a GRO-α mediated cellular event.

In another aspect, the present invention provides a method for treating a disorder selected from psoriasis, atopic dermatitis, arthritis, asthma, chronic obstructive pulmonary disease, adult respiratory distress syndrome, inflammatory bowel disease, Crohn's disease, ulcerative colitis, stroke, septic shock, endotoxic shock, gram negative sepsis, toxic shock syndrome, cardiac and renal reperfusion injury, glomerulonephritis, thrombosis, graft vs. host reaction, Alzheimer's disease, allograft rejections, malaria, restinosis, angiogenesis and undesired hematopoietic stem cells release. The method includes administering to a subject in need thereof, an amount of a nicotinamide compound of the present invention, where the amount is sufficient to treat one or more of the disorders.

In another aspect, the present invention provides a method for inhibiting IL-8 or GRO-α driven chemotaxis in a subject. The method includes administering to a subject in need thereof, through a therapeutically acceptable manner, a therapeutically effective amount of a nicotinamide compound of the invention.

In these methods, the administration may be, for example, transdermal, oral, intravenous, intramuscular, vaginal, rectal, pulmonary, subcutaneous, sublingual and transmucosal administration.

The "effective amount" or "therapeutically effective amount" of a compound of the present invention will depend on the route of administration, the type of mammal being treated, and the physical characteristics of the specific mammal under consideration. These factors and their relationship to determining this amount are well known to skilled practitioners in the medical arts. This amount and the method of administration can be tailored to achieve optimal efficacy but will depend on such factors as weight, diet, concurrent medication and other factors that those skilled in the medical arts will recognize.

In another aspect, the present invention provides a method for identifying a binding partner to a nicotinamide compound as disclosed herein, where the method comprises: immoblizing protein known to be involved in a signaling pathway of chemotaxis onto a suitable carrier; and passing a solution of said nicotinamide compounds in isolation or mixture over said protein and analyzing for compound:protein complex formation using surface plasmon resonance (SPR). This method may be performed in analogy to the method described in Karlsson, R et al. "Biosensor Analysis of Drug-Target Interactions: Direct and Competitive Binding Assays for Investigation of Interactions Between Thrombin and Thrombin Inhibitors" *Anal. Biochem.* 278(1):1–13 (2000). For other examples of identifying small molecule-protein interactions using SPR see the Biacore website: http://www.biacore.com.

In another aspect, the present invention provides a method for identifying a binding partner to a nicotinamide compound as disclosed herein, where the method comprises: contacting a cell or cell components with said nicotinamide compound in isolation or mixture; removing uncomplexed cellular material, for example by gentle washing with aqueous buffer; and recovering said binding partner from the compounds. The nicotinamide compound(s) are preferably bound to a solid support. See, e.g., methodology reported in Shimizu, N et al. "High Performance Affinity Beads for Identifying Drug Receptors" *Nature Biotechnology* 18(8): 877–881 (2000).

In another aspect, the present invention provides a solution-based method for identifying a binding partner to a nicotinamide compound as disclosed herein, where the method includes contacting a cell or cell component with said nicotinamide compound in isolation or mixture; providing a method for covalent attachment of the compound to its binding partner; and then isolating and identifying the covalently linked entities.

This covalent attachment may be accomplished using e.g., photolysis (see, for example, Steve A. Fleming, "Chemical Reagents in Photoaffinity Labeling", *Tetrahedron*, 1995, vol. 51, no 46, pp. 12479–12520), a direct alkylation step (see, for example, Gustavo R. Rosinia, et al., "Myoseverin, A Microtubule-binding Molecule With Novel Cellular Effect", *Nature Biotechnology*, 2000, vol. 18, pp. 304–308), or by other means. The isolation of the modified binding partner may take advantage of gel electrophoresis and/or autoradiography, and/or affinity purification, and/or other techniques known to one skilled in the art. The identification of the derivatized protein may be based on protein sequence analysis, tryptic digest with mass spec analysis, or other methods known to one skilled in the art. Thus, the present invention provides a method for identifying a binding partner to a nicotinamide compound as described herein comprising: contacting a cell or cell components with said compound in isolation or in mixture with other of said compounds, inducing a chemical reaction which will covalently link the compound to its binding partner, and then isolating and identifying the modified binding partner.

As to each publication or patent referenced herein, that publication or patent is incorporated herein by reference in its entirety for all purposes.

From the foregoing it will be appreciated that, although specific embodiments of the invention have been described herein for purposes of illustration, various modifications may be made without deviating from the spirit and scope of the invention. Accordingly, the invention is not limited except as by the appended claims.

The following examples are offered by way of illustration, and not by way of limitation.

EXAMPLES

Example 1

Synthesis of

N-(4-fluoro-phenyl)-6-mercapto-nicotinamide

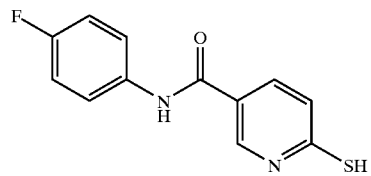

To a solution of 6-mercaptonicotinic acid (0.85 g, 5.48 mmol) in 50 mL of DMF was added 4-fluoroaniline (1.0 mL, 11.0 mmol) and 2-ethyoxy-1-ethoxycarbonyl-1,2-dihydroquinoline (EEDQ, 1.6 g, 6.6 mmol). The mixture was stirred for 30 minutes and the volatiles removed in vacuo. The resulting residue was diluted with ethyl acetate to yield a light tan solid that was isolated by vacuum filtration to give 0.63 g (47%) of the titled compound: $^1$H NMR (300 MHz, DMSO-$d_6$) δ 10.20 (s, 1H), 8.28 (m, 1H), 7.83 (m, 1H), 7.68 (m, 2H), 7.33 (m, 1H), 7.15 (m, 2H); MS (EI) m/z 247.05 (M-H)$^-$.

Example 2

Synthesis of

[5-(4-fluoro-phenylcarbamoyl)-pyridin-2-ylsulfanyl]-acetic acid propyl ester

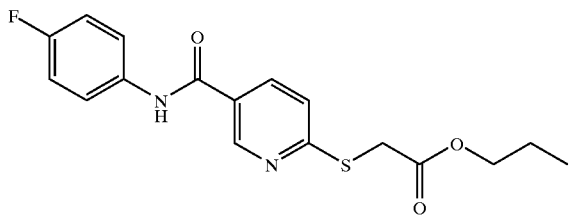

To a solution of N-(4-fluoro-phenyl)-6-mercapto-nicotinamide (0.024 g, 0.097 mmol, see Example 1) in 2 mL of DMF was added cesium carbonate (0.094 g, 0.29 mmol) and propyl bromoacetate (0.025 μL). The mixture was stirred for 30 minutes and poured into ethyl acetate and water. The organic layer was removed, dried over sodium sulfate, filtered, and the solvents removed in vacuo. Purification by trituration using ethyl acetate/hexanes gave 34 mg (76%) of the titled product as a white solid:

$^1$H NMR (300 MHz, DMSO-$d_6$) δ 10.36 (s 1H), 8.88 (m, 1H), 8.12 (m, 1H), 7.73 (m, 2H), 7.49 (m, 1H), 7.18 (m, 2H), 4.09 (s, 2H), 4.02 (m, 2H), 1.54 (m, 2H), 0.82 (m, 3H); MS (EI) m/z 347.06 (M-H)$^-$.

Example 3

Synthesis of

[5-(2-azido-phenylcarbamoyl)-pyridin-2-ylsulfanyl]-acetic acid ethyl ester

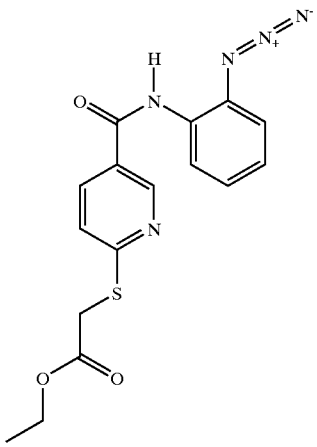

A. To a mixture of 2-nitroaniline (1 g, 7.23 mmol) in acetic acid (5 mL) was added phthalic anhydride (1.29 g, 8.7 mmol) followed by stirring at ambient temperature for 16 h. The mixture was then heated at reflux for 20 h. Upon cooling, a yellow precipitate formed and was collected by filtration. The filtrate was washed with acetic acid and was dried under a under a stream of air to give 2.35 g (100%) of 2-(2-nitrophenyl)isoindole-1,3-dione: $^1$H NMR (300 MHz, DMSO-$d_6$) δ8 8.21 (m, 1H), 8.02-7.95 (m, 5H), 7.77 (m, 2H).

B. To a suspension of the 2-(2-nitrophenyl)isoindole-1,3-dione (1.0 g, 3.50 mmol) in benzene, pre-sparged with nitrogen gas, was added 10% palladium on activated carbon (1.0 g). The reaction mixture was placed under an atmosphere of hydrogen gas and was vigorously stirred. After 45 minutes, the reaction mixture was filtered over celite and the filter pad was washed with benzene. Concentration in vacuo gave 236 mg (40%) of 2-(2-aminophenyl)-isoindole-1,3-dione as a yellow solid: $^1$H NMR (300 MHz, DMSO-$d_6$) δ 8.85 (m, 4H), 7.10 (m, 1H), 6.98 (m, 1H), 6.75 (m, 1H), 6.55 (m, 1H).

C. To a suspension of the 2-(2-aminophenyl)isoindole-1,3-dione (360 mg, 1.5 mmol) in acetic acid (20 mL) and water (4 mL) was added dropwise a solution of sodium nitrite (98 mg, 1.42 mmol) in water (2 mL). The mixture was allowed to stir for 10 minutes and then sodium azide (98 mg, 1.51 mmol) was added. The reaction mixture was stirred for 15 minutes before it was poured into water and was extracted with dichloromethane (3×50 mL). The extracts were washed with water and brine and dried over magnesium sulfate. Filtration and concentration in vacuo gave 373 mg (94%) of 2-(2-azidophenyl)isoindole-1,3-dione as a solid: $^1$H NMR (300 MHz, DMSO-$d_6$) δ 7.94 (m, 4H), 7.58 (m, 1H), 7.48 (m, 2H), 7.32 (m, 1H).

D. To a suspension of the of 2-(2-azido-phenyl)-isoindole-1,3-dione (373 mg, 1.4 mmol) in ethanol (10 mL) was added hydrazine (140 μL, 4.24 mmol) followed by stirring for 15 minutes. The reaction mixture was poured into water and was extracted with ethyl acetate (3×25 mL). The combined extracts were washed with water and brine and were dried over magnesium sulfate. Filtration and concentration in vacuo gave a residue which was purified via radial chromatography (1 mm plate, 10% 5ethyl acetate/hexanes to 33% ethyl acetate/hexanes gradient elution) to give 48 mg (25%) of 2-azidophenylamine as a solid: $^1$H NMR (300 MHz, DMSO-$d_6$) δ 6.98 (m, 1H), 6.86 (m, 1H), 6.66–6.55 (m, 2H).

E. To a mixture of 2-mercaptonicotinic acid (53 mg, 0.34 mmol) and 2-azidophenylamine (45 mg, 0.34 mmol) in DMF (3 mL) was added EEDQ (101 mg, 0.41 mmol) followed by stirring at an ambient temperature for 15 h. The mixture was poured into water and the resulting suspension was extracted with ethyl acetate (3×25 mL). The combined extracts were washed with water and brine and dried over magnesium sulfate. Filtration and concentration gave 40 mg of a residue which was not characterized or purified, but was directly dissolved in NMP (3 mL) and treated with ethyl bromoacetate (35 μL, 0.3 mmol) in the presence of DIPEA (80 L, 0.45 mmol). After stirring for 15 minutes, the mixture was poured into water and was extracted with ethyl acetate (3×25 mL). The combined extracts were washed with water and brine and dried over magnesium sulfate. Filtration and concentration gave a residue that was purified via radial chromatography to afford 9.1 mg (7.5% two steps) of [5-(2-azidophenylcarbamoyl)-pyridin-2-ylsulfanyl]-acetic acid ethyl ester as a solid: $^1$H NMR (300 MHz, acetone-$d_6$) δ 8.98 (d, J=1.6 Hz, 1H), 8.16 (m, 2H), 7.47 (d, J=8.2 Hz, 1H), 7.35–7.18 (m, 3H), 4.15 (q, J=7.14 Hz, 2H), 4.09 (s, 2H), 1.22 (s, 3H); MS (EI) m/z 355.92 (M–H)$^-$.

Example 4

Synthesis of

[5-(2-azido-4-fluoro-phenylcarbamoyl)-pyridin-2-ylsulfanyl]-acetic acid ethyl ester The titled compound was synthesized in a manner analogous to the synthesis of [5-(2-azido-phenylcarbamoyl)-pyridin-2-ylsulfanyl]-acetic acid ethyl ester as set forth in Example 3. The titled compound was characterized by mass spectrometry: MS (EI) m/z 374.13 (M–H)$^-$.

Example 5

Synthesis of

[5-(3-azido-4-fluoro-phenylcarbamoyl)-pyridin-2-ylsulfanyl]-acetic acid ethyl ester

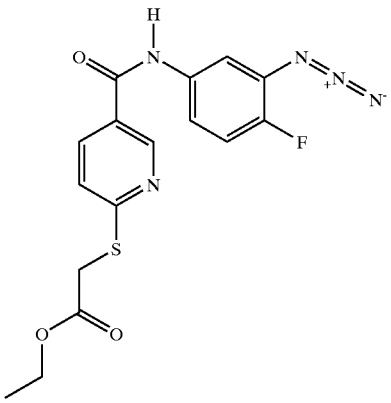

A. To a mixture of 2-mercaptonicotinic acid (0.5 g, 3.22 mmol) and 4-fluoro-3-nitro-phenylamine (1.0 g, 6.44 mmol) in DMF (20 mL) was added EEDQ (954 mg, 3.86 mmol).

The reaction mixture was stirred at an ambient temperature for 15 h and was poured into water. The resulting yellow solids were isolated by filtration through a fritted glass funnel. The solids were rinsed from the filter with ethyl acetate (20 mL) and the resulting suspension was heated briefly (1 minute) before cooling and filtering. This gave 282 mg (25%) of N-(4-fluoro-3-nitro-phenyl)-6-mercapto-nicotinamide as a yellow solid: $^1$H NMR (300 MHz, DMSO-d$_6$) δ 10.54 (s, 1H), 8.58 (m, 1H), 8.32 (bs, 1H), 8.03 (m, 1H), 7.84 (m, 1H), 7.57 (m, 1H), 7.35 (m, 1H).

B. To mixture of the of N-(4-fluoro-3-nitro-phenyl)-6-mercapto-nicotinamide (200 mg, 0.68 mmol) and ethyl bromoacetate (113 μL, 1.02 mmol) in DMF (5 mL) was added DIPEA (243 μL, 1.4 mmol). The reaction mixture was stirred for 10 minutes before being poured into water and being extracted with ethyl acetate (3×50 mL). The combined extracts were washed with water and brine and were dried over magnesium sulfate. Filtration followed by concentration in vacuo gave 278 mg (100%) of [5-(4-fluoro-3-nitro-phenylcarbamoyl)-pyridin-2-ylsulfanyl]-acetic acid ethyl ester as a solid: $^1$H NMR (300 MHz, acetone-d$_6$) δ 10.0 (bs, 1H), 9.02 (m, 1H), 8.21 (m, 1H), 8.18 (m, 2H, 7.46 (m, 2H), 4.16 (m, 2H) (s, 2H), 1.22 (m, 3H); MS (EI) m/z 377.88 (M–H)$^-$.

To a mixture of the 5-(4-fluoro-3-nitro-phenylcarbamoyl)-pyridin-2-ylsulfanyl]acetic acid ethyl ester (278 mg) in ethanol (50 mL), pre-sparged with nitrogen gas, was added 10% palladium on activated carbon (300 mg). The reaction mixture was placed under an atmosphere of hydrogen gas and stirred vigorously for 4 h. The mixture was filtered through a plug of celite and the filter pad was washed with ethanol. The mixture was concentration in vacuo, was redissolved in ethyl acetate and was passed through a plug of silica gel and eluted with additional ethyl acetate. The resulting solution was again concentration in vacuo, and was further purified via radial chromatography to give 84 mg of the [5-(3-amino-4-fluoro-phenylcarbamoyl)-pyridin-2-ylsulfanyl]-acetic acid ethyl ester as a mixture with other unidentified material. The [5-(3-amino-4-fluoro-phenyl-carbamoyl)pyridin-2-ylsulfanyl]-acetic acid ethyl ester was not characterized, but was carried on directly. The material was dissolved in a mixture of acetic acid and water (5:1, 6 mL total volume) and the mixture was cooled in an ice-water bath. A solution of sodium nitrate (33 mg) in water (0.5 mL) was following stirring for 10 minutes neat sodium azide (31 mg) was added. The mixture was stirred for an additional 2 h and was diluted with water and extracted with ethyl acetate (3×50 mL). The combined extracts were washed with brine and dried over magnesium sulfate. The extracts were filtered and concentrated under reduced pressure and the resulting residue was purified via radial chromatography (1 mm plate, 10% ethyl acetate/hexanes to 33% ethyl acetate/hexane gradient elution). Product containing fractions were collected and concentrated. The resulting residue was dissolved in ethyl acetate and precipitated with hexanes to give a solid that was collected via filtration on a fritted glass funnel. This afforded 23 mg (9% for three steps) of [5-(3-azido-4-fluoro-phenylcarbamoyl)-pyridin-2-ylsulfanyl]-acetic acid ethyl ester: $^1$H NMR (300 MHz, DMSO-d$_6$) δ 10.44 (s, 1H), 8.90 (m, 1H), 8.15 (m, 1 h), 7.78 (m, 1H), 7.49 (m, 2H), 7.30 (m, 1H), 4.08 (m, 4H), 1.16 (m, 3H (EI) m/z 373.91 (M–H)$^-$.

Example 6

Synthesis of

[5-(3-azido-phenylcarbamoyl)-pyridin-2-ylsulfanyl]-acetic acid ethyl ester

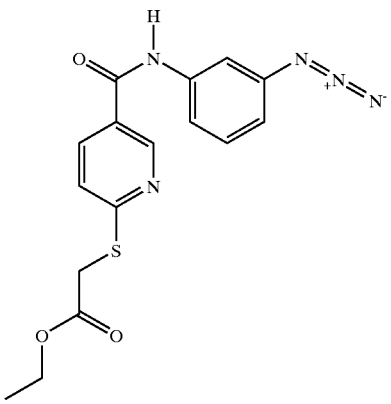

A. To a mixture of benzene-1,3-diamine (1.0 g, 18.5 mmol) in DCM (25 mL) was added BOC anhydride (3.2 ml, 27.8 mmol) and the mixture was stirred for 15 h at an ambient temperature. The mixture was concentration in vacuo and the mono-carbamate was separated from the mixture via radial chromatography (4 mm plate, 10% ethyl acetate/hexanes to 33% ethyl acetate/hexanes gradient elution) to give 219 mg (11%) of (3-amino-phenyl)-carbamic acid tert-butyl ester as a white solid: $^1$H NMR (300 MHz, DMSO-d$_6$) δ 8.95 (bs, 1H), 6.80 (m, 2H), 6.48 (m, 1H), 6.15 (m, 1H), 5.95 (bs, 1H), 1.42 (s, 9H).

B. To a mixture of the (3-amino-phenyl)-carbamic acid tert-butyl ester (100 mg, 0.48 mmol) and 2-mercaptonicotinic acid (81 mg, 0.52 mmol) in DMF (5 mL) was added EEDQ (154 mg, 0.63 mmol). The mixture was stirred at ambient temperature for 15 h, was diluted with water and extracted with ethyl acetate (3×25 mL). The combined extracts were washed with water and brine and dried over magnesium sulfate. The residue was taken up in a small quantity of ethyl acetate (3 mL) and was briefly heated at reflux (1 minute). The mixture was cooled and the resulting solids collected via vacuum filtration on a fritted glass funnel. This afforded 90 mg of a solid which was not purified or characterized, but carried on directly. The material was dissolved in NMP (5 mL) and was treated with ethyl bromoacetate (32 μL, 0.29 mmol) and DIPEA (90 μL, 0.52 mmol). The resulting mixture was stirred for 10 minutes and was poured into water. The resulting mixture was extracted with ethyl acetate (3×50 mL) and the combined extracts were washed with water and brine. Filtration and concentration in vacuo afforded a residue which was purified via radial chromatography (1 mm plate, 10% ethyl acetate/hexanes) to give 41 mg (36%) of [5-(3-tert-butoxycarbonylamino-phenylcarbamrloyl)-pyridin-2-ylsulfanyl]-acetic acid ethyl ester as a solid: $^1$H NMR (300 MHz, acetone-d$_6$) δ 9.63 (bs, 1H), 8.99 (m, 1H), 8.45 (bs,1H), 8.18 (m, 1H), 8.01 (s, 1H), 7.58 (m, 1H), 7.40 (m, 1H), 7.20 (m, 2H), 4.13 (m, 2H), 4.07 (s, 2H), 1.47 (s, 9H), 1.19 (m, 1H); MS (EI) m/z 430.06 (M–H)$^-$.

C. To a 0° C. solution of [5-(3-tert-butoxycarbonylaminophenyl-carbamoyl)pyridin-2-ylsulfanyl]-acetic acid ethyl ester (41 mg, 0.10 mmol) in DCM (3 mL) was added TFA (3 mL) followed by stirring for 15 minutes. The mixture was concentrated in vacuo and was taken up in a mixture of acetic acid (3 mL) and water (1 mL), cooled to 0° C., and treated with a solution of sodium nitrite (15 mg, 0.23 mmol) in water (1 mL). After 5 minutes, the mixture was treated with neat sodium azide (15 mg, 0.22 mmol) and the solution was allowed to warm to an ambient temperature over 30 minutes. The mixture was poured into water and was extracted with ethyl acetate (3×25 mL) and the combined extracts were washed with water and brine and dried over magnesium sulfate. Filtration and concentration gave 42.4 mg (100%) of the [5-(3-azido-phenylcarbamoyl)-pyridin-2-ylsulfanyl]-acetic acid ethyl ester as a solid: $^1$H NMR (300 MHz, acetone-d$_6$) δ 9.73 (bs, 1H), 8.98 (m, 1H), 8.18 (m, 1H), 7.75 (m, 1H), 7.60 (m, 1H), 7.45 (m, 1H, 7.39 (m, 1H), 6.85 (m, 1H), 4.15 (m, 2H), 4.07 (s, 2H), 1.22 (m, 3H); MS (EI) m/z 356.11 (M–H)$^-$.

Example 7

Synthesis of

[5-(4-azido-phenylcarbamoyl)-pyridin-2-ylsulfanyl]-acetic acid ethyl ester

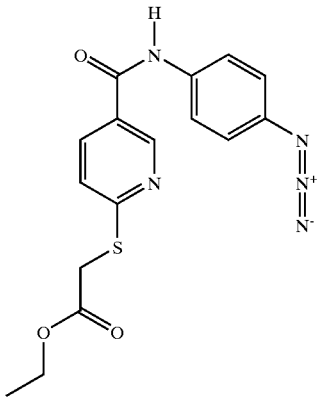

A. To a mixture of 2-mercaptonicotinic acid (100 mg, 0.65 mmol) in DMF (5 mL) was added EEDQ (207 mg, 0.84 mmol). The resulting mixture was stirred for 10 minutes, followed by the addition of a premixed solution of 4-azido-phenyl-ammonium chloride (219 mg, 1.29 mmol) and DIPEA (224 uL, 1.29 mmol) in DMF (2 mL). The mixture was allowed to stir for 15 h and was poured into ethyl acetate. The resulting solution was washed with 0.1 N hydrochloric acid, water and brine. The organic phase was dried over magnesium sulfate, was filtered and concentration in vacuo. The resulting residue was taken up in ethyl acetate (10 mL) and solids were precipitated through the addition of hexanes. The solids were collected by filtration (92 mg) and were used directly without purification or characterization. The solids were dissolved in DMF (5 mL), ethyl bromoacetate (75 μL, 0.68 mmol) was added, followed by the addition of cesium carbonate (332 mg, 1.02 mmol). The reaction mixture was stirred for 15 minutes, poured into water and the resulting precipitate was collected via vacuum filtration on a fritted glass funnel. The solids were washed off the filter with ethyl acetate and the mixture was dried with magnesium sulfate. Filtration and concentration in vacuo gave a residue that was dissolved in ethyl acetate (10 mL). The solution was treated with hexanes and cooled resulting in precipitation of [5-(4-azido-phenylcarbamoyl)-pyridin-2-ylsulfanyl]-acetic acid ethyl ester, 46 mg (20% for two steps), isolated by filtration: $^1$H NMR (300 MHz, DMSO-d$_6$) δ 10.38 (bs, 1H), 8.89 (m, 1H), 8.14 (m, 1H), 7.77 (m, 2H), 7.49 (m, 1H),7.12 (m, 2H), 4.10 (m, 4H), 1.16 (m, 3H); MS (EI) m/z 356.11 (M–H)$^-$.

Example 8

Synthesis of

[5-(4-iodo-phenylcarbamoyl)-pyridin-2-ylsulfanyl]-acetic acid ethyl ester

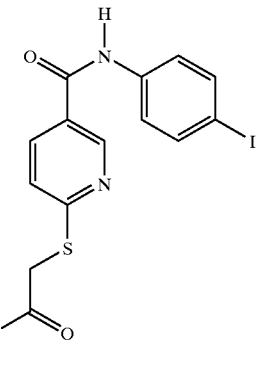

To a mixture of 2-mercaptonicotinic acid (200 mg, 1.29 mmol) and 4-iodoaniline (340 mg, 1.75 mmol) in DMF (5 mL) was added EEDQ (415 mg, 1.68 mmol) followed by stirring at an ambient temperature for 15 h. The mixture was poured into water and the resulting precipitate was collected via vacuum filtration on a fritted glass funnel. The precipitate was dried under a continuous stream of air to give 194 mg of a solid that was used without purification or characterization. The material was dissolved in NMP (5 mL) and was treated with ethyl bromoacetate (73 μL, 0.65 mmol) and DIPEA (280 μL, 1.64 mmol). After 1 h, the mixture was poured into water and was extracted with ethyl acetate (3×50 mL). The combined extracts were washed with water and brine and were dried over magnesium sulfate. Filtration and concentration in vacuo gave a residue that was purified via radial chromatography (1 mm plate, 33% ethyl acetate/hexanes as eluant).

This afforded 80 mg (14% for two steps) of the [5-(4-iodo-phenylcarbamoyl)-pyridin-2-ylsulfanyl]-acetic acid ethyl ester as a solid: $^1$H NMR (300 MHz, DMSO-d$_6$) δ 10.4 (bs, 1H), 8.89 (m, 1H), 8.12 (m, 1H), 7.63 (m, 2H), 7.58 (m, 2H), 7.49 (m, 1H), 4.07 (m, 4H), 1.16 (m, 3H); MS (EI) m/z 440.86 M–H)$^-$.

Examples 9A–9C

The following compounds were synthesized in a manner similar to [5-(4-iodo-phenylcarbamoyl)-pyridin-2-ylsulfanyl]-acetic acid ethyl ester as described in Example 8:

9A. [5-(3-iodo-phenylcarbamoylypyridin-2-ylsulfanyl]-acetic acid ethyl ester; MS (EI) m/z 440.84 (M–H)$^-$.

9B. [5-(3-iodo-4-methyl-phenylcarbamoyl)-pyridin-2-ylsulfanyl]-acetic acid ethyl ester; MS (EI) m/z 454.73 (M–H)$^-$.

9C. [5-(2-tert-butoxycarbonylamino-phenylcarbamoylypyridin-2-ylsulfanyl]-acetic acid ethyl ester; MS (EI) m/z 430.05 (M–H)$^-$.

Example 10

Synthesis of 6-chloro-N-(4-fluoro-phenyl)-nicotinamide

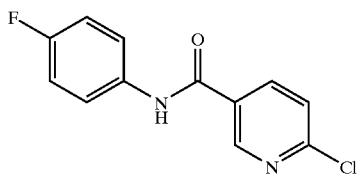

To a suspension of 6-chloronicotinoyl chloride (10.5 g, 59.7 mmole) in dry dichloromethane (100 mL) was added 4-fluoroaniline (5.6 mL, 59.7 mmole), followed by the dropwise addition of N,N-diisopropylethylamine (21 mL, 19 mmol).

After stirring for 90 minutes at room temperature, the mixture was diluted with ethyl acetate (20 mL) and washed with water. The combined organic extracts were dried over anhydrous sodium sulfate, filtered, and concentrated in vacuo. Purification by recrystallization using ethyl acetate/hexanes gave 13.8 g (92%) of a white solid. $^1$H NMR (300 MHz, CDCl$_3$) δ 7.09–7.12 (m, 2H), 7.47–7.50 (m, 1H), 7.56–60 (m, 2H), 7.7 (bs, 1H), 8.15–8.18 (m, 1H), 8.84 (m, 1H); MS (EI) m/z 251.13 (M+H)$^+$.

Example 11

Synthesis of

[5-(4-fluoro-phenylcarbamoyl)-pyridin-2-ylsulfanyl]-acetic acid ethyl ester

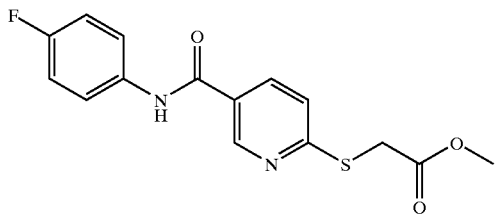

To a solution of 6-chloro-N-(4-fluoro-phenyl)-nicotinamide (0.21 g, 0.84 mmol) in 5 mL of THF was added potassium tert-butoxide (0.19 g, 1.68 mmol) in one portion and stirred for 1 minute. To the suspension was added methyl thioglycolate (0.15 mL, 1.68 mmol) dropwise over 1 minute. The mixture was stirred for 12 h then poured into ice water and the solids collected. Purification by trituration using ethyl acetate/hexanes gave 88 mg (33%) of the desired product as a white solid: $^1$H NMR (300 MHz, DMSO-d$_6$) δ 10.36 (s 1H), 8.90 (m, 1H), 8.11 (m, 1H), 7.74 (m, 2H), 7.48 (m, 1H), 7.17 (m, 2H), 4.10 (s, 2H), 3.63 (s, 3H); MS (EI) m/z 319.13 (M–H)$^-$.

Example 12

Synthesis of 6-bromo-N-(4-fluoro-phenyl)-nicotinamide

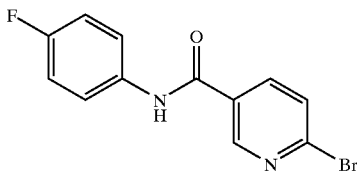

To a suspension of 6-bromonicotinoyl chloride (0.5 g, 2.5 mmol) in dry chloroform (10 mL) was added 4-fluoroaniline (0.33 mL, 3.5 mmol) and 2-ethyoxy-1-ethoxycarbonyl-1,2-dihydroquinoline, (0.85 g, 3.5 mmol). The mixture was stirred for 12 h, diluted with hexanes and the solids isolated by filtration. Purification by trituration using ethyl acetate/hexanes gave 0.53 g (73%) of the desired product as a white solid. $^1$H NMR (300 MHz, DMSO-d$_6$) a 10.51 (s, 1H), 8.87 (m, 1H), 8.20 (m, 1H), 7.82 (m, 1H), 7.74 (m, 2H), 7.19 (m, 2H).

Example 13

Synthesis of

[5-(4-fluoro-phenylcarbamoyl)-pyridin-2-yloxy]-acetic acid methyl ester

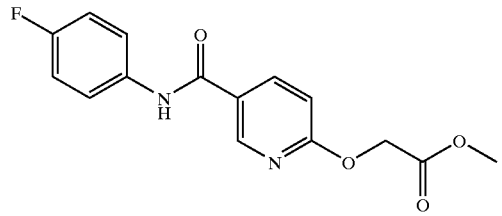

A suspension of 6-bromo-N-(4-fluoro-phenyl) nicotinamide (1.0 g, 3.4 mmol), methyl glycolate (1.6 mL, 19 mmol), and potassium tert-butoxide (1.5 g, 10 13.6 mmol) in THF (10 mL) was heated in a sealed tube at 70° C. After 3 h the reaction mixture was poured onto ice and the solids isolated by filtration. Purification on silica gel by column chromatography using 30% ethyl acetate in hexanes gave 0.68 g (65%) of the titled product as a white solid:

$^1$H NMR (300 MHz, DMSO-d$_6$) δ 10.30 (s 1H), 8.66 (m, 1H), 8.22 (m, 1H), 7.73 (m, 2H), 7.16 (m, 2H), 7.04 (m, 1H), 4.98 (s, 2H), 3.65 (s, 3H); MS (EI) m/z 303.13 (M–H)$^-$.

Example 14

Synthesis of

[5-(4-fluoro-phenylcarbamoyl)-pyridin-2-yloxy]-acetic acid

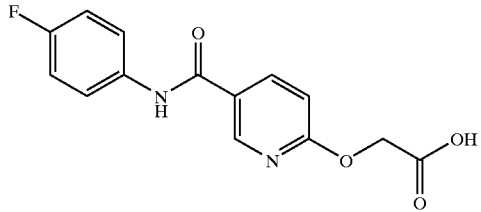

To a solution of [5-(4-fluoro-phenylcarbamoyl)-pyridin-2-yloxy]-acetic acid methyl ester (0.052 g, 0.17 mmol) in THF (1.2 mL) was added an aqueous solution of sodium hydroxide (0.34 mL of a 1 M solution, 0.34 mmol). After 30 minutes the reaction was acidified to pH 3 with 6N HCl and the solvent removed in vacuo. The solids were washed with cold water and the volatiles removed to yield 0.43 g (82%) of the titled product as a white solid:

$^1$H NMR (300 MHz, DMSO-$d_6$) δ 10.29 (s, 1H), 8.67 (m, 1H), 8.20 (m, 1H), 7.71 (m, 2H), 7.17 (m, 2H), 7.00 (m, 1H), 4.88 (m, 2H); MS (EI) m/z 289.06 (M–H)$^-$.

Example 15

Synthesis of

[5-(4-fluoro-phenylcarbamoyl)-pyridin-2-yloxy]-acetic acid ethyl ester

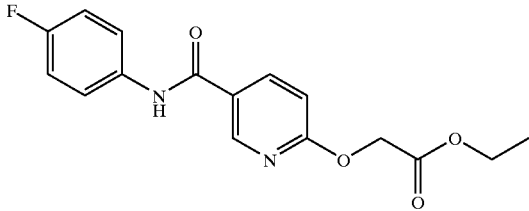

A solution of [5-(4-fluoro-phenylcarbamoyl)-pyridin-2-yloxy]-acetic acid methyl ester (0.030 g, 0.99 mmole), ethanol (2 mL), and sulfuric acid (1 drop) was heated in a sealed tube at 80° C. After 6 h the reaction mixture was poured into ethyl acetate and washed with saturated sodium bicarbonate and dried over sodium sulfate. Removal of the solvents provided 6 mg (20%) of the titled product as a white solid:

$^1$H NMR (300 MHz, DMSO-$d_6$) δ 10.30 (s 1H), 8.66 (m, 1H), 8.22 (m, 1H), 7.73 (m, 2H), 7.16 (m, 2H), 7.04 (m, 1H), 4.96 (s, 2H); 4.11 (m, 2H); 1.16 (m, 3H); MS (EI) m/z 317.17 (M–H)$^-$.

Examples 16A–16D

The following compounds were synthesized in a manner similar to [5-(4-fluoro-phenylcarbamoyl)-pyridin-2-yloxy]-acetic acid methyl ester as described in Example 15:

16A. [5-(4-fluoro-phenylcarbamoyl)-pyridin-2-yloxy]-acetic acid butyl ester; MS (EI) m/z 345.18 (M–H)$^-$.

16B. [5-(4-fluoro-phenylcarbamoyl)-pyridin-2-yloxy]-acetic acid 3-methylbutyl ester; MS (EI) m/z 359.20 (M–H)$^-$.

16C. [5-(4-fluoro-phenylcarbamoyl)-pyridin-2-yloxy]-acetic acid propyl ester; MS (EI) m/z 331.16 (M–H)$^-$.

16D. [5-(4-fluoro-phenylcarbamoyl)-pyridin-2-yloxy]-acetic acid isopropyl ester; MS (EI) m/z 331.09 (M–H)$^-$.

Example 17

Synthesis of

[5-(4-fluoro-phenylcarbamoyl)-pyridin-2-yloxy]-acetic acid phenethyl ester

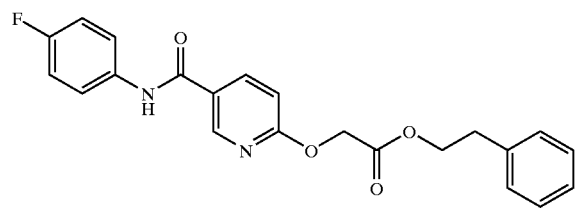

A solution of [5-(4-fluoro-phenylcarbamoyl)-pyridin-2-yloxy]-acetic acid methyl ester (0.020 g, 0.66 mmol), phenethyl alcohol (0.078 mL, 0.66 mmol) and sulfuric acid (1 drop) in toluene (3 mL) was heated at reflux. After 4 h the reaction mixture was poured into ethyl acetate and washed with saturated sodium bicarbonate and dried over sodium sulfate. Removal of the solvents provided a solid. Purification by trituration using ethyl acetate/hexanes gave 0.011 g (42%) of the titled product as a white solid: $^1$H NMR (300 MHz, DMSO-$d_6$) δ 10.29 (s 1H); 8.65 (m, 1H); 8.23 (m, 1H); 7.74 (m, 2H); 7.01–7.27 (m, 8H); 4.94 (s, 2H); 4.27 (m, 2H); 2.85 (m, 2H); MS (EI) m/z 393.03 (M–H)$^-$.

Examples 18A–18P

The following compounds were synthesized in a manner similar to [5-(4-fluoro-phenylcarbamoyl)-pyridin-2-yloxy]-acetic acid phenethyl ester as described in Example 17:

18A. [5-(4-fluoro-phenylcarbamoyl)-pyridin-2-yloxy]-acetic acid cyclohexyl ester; MS (EI) m/z 371.13 (M–H)$^-$.

18B. [5-(4-fluoro-phenylcarbamoyl)-pyridin-2-yloxy]-acetic acid benzyl ester; MS (EI) m/z 379.19 (M–H)$^-$.

18C. [5-(4-fluoro-phenylcarbamoyl)-pyridin-2-yloxy]-acetic acid 3-fluoro-benzyl ester; MS (EI) m/z 397.20 (M–H)$^-$.

18D. [5-(4-fluoro-phenylcarbamoyl)-pyridin-2-yloxy]-acetic acid 4-cyclohexyl-butyl ester; MS (EI) m/z 427.30 (M–H)$^-$.

18E. [5-(4-fluoro-phenylcarbamoyl)-pyridin-2-yloxy]-acetic acid pentafluorophenylmethyl ester; MS (EI) m/z 469.07 (M–H)$^-$.

18F. [5-(4-fluoro-phenylcarbamoyl)-pyridin-2-yloxy]-acetic acid cyclopentyl ester; MS (EI) m/z 357.21 (M–H)$^-$.

18G. [5-(4-fluoro-phenylcarbamoyl)-pyridin-2-yloxy]-acetic acid cyclobutylmethyl ester; MS (EI) m/z 357.24 (M–H)$^-$.

18H. [5-(4-fluoro-phenylcarbamoyl)-pyridin-2-yloxy]-acetic acid cyclopropylmethyl ester; MS (EI) m/z 343.20 (M–H)$^-$.

18I. [5-(4-fluoro-phenylcarbamoyl)-pyridin-2-yloxy]-acetic acid 2-cyclohexyloxy-ethyl ester; MS (EI) m/z 415.21 (M–H)$^-$.

18J. [5-(4-fluoro-phenylcarbamoyl)-pyridin-2-yloxy]-acetic acid 4-bromo-benzyl ester; MS (EI) m/z 459.00 (M–H)$^-$.

18K. [5-(4-fluoro-phenylcarbamoyl)-pyridin-2-yloxy]-acetic acid 2-fluoro-benzyl ester; MS (EI) m/z 397.19 (M−H)⁻.

18L. [5-(4-fluoro-phenylcarbamoyl)-pyridin-2-yloxy]-acetic acid 3-bromo-benzyl ester; MS (EI) m/z 459.10 (M−H)⁻.

18M. [5-(4-fluoro-phenylcarbamoyl)-pyridin-2-yloxy]-acetic acid 3-chloro-benzyl ester; MS (EI) m/z 413.15 (M−H)⁻.

18N. [5-(4-fluoro-phenylcarbamoyl)-pyridin-2-yloxy]-acetic acid 2-bromo-benzyl ester; MS (EI) m/z 459.06 (M+H)⁻.

18O. [5-(4-fluoro-phenylcarbamoyl)-pyridin-2-yloxy]-acetic acid 4-chloro-benzyl ester; MS (EI) m/z 413.16 (M−H)⁻.

18P. [5-(4-fluoro-phenylcarbamoyl)-pyridin-2-yloxy]-acetic acid phenyl ester; MS (EI) m/z 365.06 (M−H)⁻.

Example 19

Synthesis of sodium; [5-(4-fluoro-phenylcarbamoyl)-pyridin-2-ylsulfanyl]-acetate

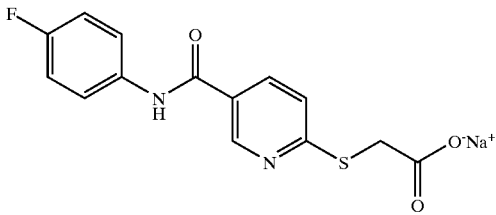

To a stirred solution of [5-(4-fluoro-phenylcarbamoyl)-pyridin-2-ylsulfanyl]-acetic acid methyl ester (2.8 g, 8.75 mmol) in THF (61 mL) was added ethyl alcohol (12 mL) and NaOH (18 mL of a 1 M aqueous solution). After 20 minutes the solids were collected and washed with THF (2×100 mL) to give 2.9 g (100%) of the titled product as a white solid.

Example 20

Synthesis of 5-(4-fluoro-phenylcarbamoyl)-pyridin-2-ylsulfanyl]-acetic acid

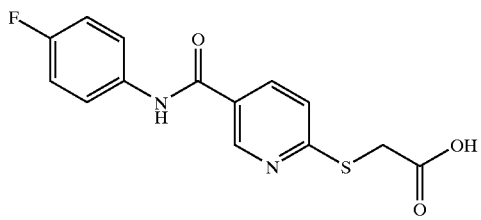

Sodium; [5-(4-fluoro-phenylcarbamoyl)-pyridin-2-ylsulfanyl]-acetate (2.9 g) was taken into water (300 mL), acidified with HCl (conc.) to pH 4.5, and collected by filtration to yield 2.4 g of the product as a white solid: ¹H NMR (300 MHz, DMSO-d₆) δ 10.40 (s 1H); 8.86 (m, 1H); 8.06 (m, 1H); 7.75 (m, 2H); 7.34 (m, 1H); 7.16 (m, 2H); 3.67 (s, 2H); MS (EI) m/z 305.02 (M−H)⁻.

Example 21

Synthesis of

N-(4-fluoro-phenyl)-6-propylcarbamoylmethylsulfanyl-nicotinamide

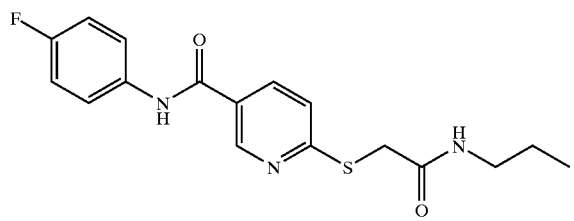

To a suspension of 5-(4-fluoro-phenylcarbamoyl)-pyridin-2-ylsulfanyl]-acetic acid (0.030 g, 0.10 mmol) and propylamine (41 μL, 0.50 mmol) in DMF (1 mL) was added bromo-tris-pyrrolidino-phosphonium hexafluorophosphate (0.060 g, 0.13 mmol). After 12 h the reaction mixture was poured into cold water and the solids collected. Purification by trituration using ethyl acetate/hexanes gave 0.011 g (32%) of the titled product as a white solid:

¹H NMR (300 MHz, DMSO-d₆) δ 10.36 (s, 1H); 8.89 (m, 1H); 8.11 (m, 2H); 7.73 (m, 2H); 7.46 (m, 1H); 7.17 (m, 2H); 3.88 (s, 2H); 2.99 (m, 2H); 1.37 (m, 2H); 0.79 (m, 3H); MS (EI) m/z 346.16 (M−H)⁻.

Examples 22A-22I

The following compounds were made in the same manner as N-(4-fluoro-phenyl)-6-propylcarbamoylmethylsulfanyl-nicotinamide as described in Example 21:

22A. N-(4-fluoro-phenyl)-6-methylcarbamoylmethylsulfanyl-nicotinamide; MS (EI) m/z 318.19 (M−H)⁻.

22B. 6-diethylcarbamoylmethylsulfanyl-N-(4-fluoro-phenyl)-nicotinamide; MS (EI) m/z 360.21 (M−H)⁻.

22C. N-(4-fluoro-phenyl)-6-[(3-hydroxy-propylcarbamoyl)-methyl-sulfanyl]-nicotinamide; MS (EI) m/z 348.18 (M−H)⁻.

22D. 6-carbamoylmethylsulfanyl-N-(4-fluoro-phenyl)-nicotinamide; MS (EI) m/z 304.16 (M−H)⁻.

22E. 6-dimethylcarbamoylmethylsulfanyl-N-(4-fluoro-phenyl)-nicotinamide; MS (EI) m/z 332.23 (M−H)⁻.

22F. N-(4-fluoro-phenyl)-6-phenylcarbamoylmethylsulfanyl-nicotinamide; MS (EI) m/z 380.24 (M−H)⁻.

22G. 6-cyclopentylcarbamoylmethylsulfanyl-N-(4-fluoro-phenyl)-nicotinamide; MS (EI) m/z 372.25 (M−H)⁻.

22H. N-(4-fluoro-phenyl)-6-[(4-fluoro-phenylcarbamoyl)-methylsulfanyl]-nicotinamide; MS (EI) m/z 398.18 (M−H)⁻.

22I. N-(4-fluoro-phenyl)-6-[(methyl-phenyl-carbamoyl)-methylsulfanyl]-nicotinamide; MS (EI) m/z 394.23 (M−H)⁻.

Example 23

Synthesis of

[N-(4-fluoro-phenyl)-6-(pyridin-3-ylcarbamoylmethylsulfanyl)-nicotinamide

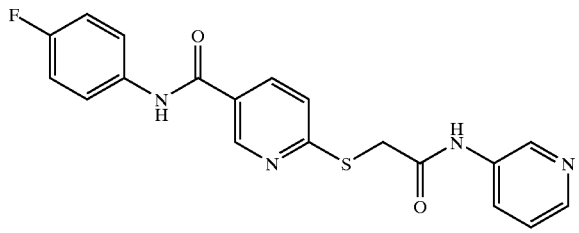

To a suspension of 5-(4-fluoro-phenylcarbamoyl)-pyridin-2-ylsulfanyl)-acetic acid (0.100 g, 0.33 mmol) and 3-aminopyridine (0.93 g, 0.99 mmol) in DMF (1 mL) was added bromo-tris-pyrrolidino-phosphonium hexafluorophosphate (0.060 g, 0.13 mmol).

After 12 h the volatiles were removed in vacuo and the solids purified by HPLC to yield 4 mg (4%) of the titled product as the TFA salt; MS (EI) m/z 381.22 (M−H)⁻.

Example 24

Synthesis of

6-[(3-Bromo-phenylcarbamoyl)-methylsulfanyl]-N-(4-fluoro-phenyl)-nicotinamide

The titled compound was made in an analogous manner to the preparation of N-(4-fluoro-phenyl)-6-(pyridin-3-ylcarbamoylmethylsulfanyl)-nicotinamide as described in Example 23, and was characterized as follows: MS (EI) m/z 459.94 (M−H)⁻.

Example 25

Synthesis of

3-[5-(4-fluoro-phenylcarbamoyl)-pyridin-2-ylsulfanyl]-propionic acid methyl ester

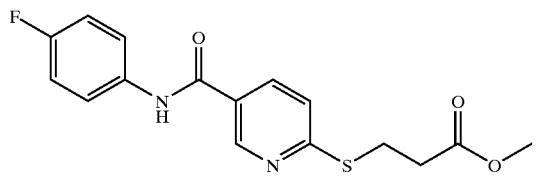

To a solution of 6-chloro-N-(4-fluoro-phenyl)-nicotinamide (0.25 g, 1.0 mmol) in 3 mL of THF was added methyl 3-mercaptopropionate (0.16 mL, 1.5 mmol) then potassium tert-butoxide (0.22 g, 2.0 mmol). The mixture was stirred for 3 h then poured into ice water and the solids washed with water and collected. Purification by trituration using ethyl acetate gave 13 mg (4%) of the titled product as a white solid: $^1$H NMR (300 MHz, DMSO-d$_6$) δ 10.33 (s, 1H), 8.94 (m,1H), 8.09 (m, 1H), 7.74 (m, 2H), 7.43 (m, 1H), 7.17 (m, 2H), 3.59 (s, 3H), 3.37 (m, 2H), 2.75 (m, 2H); MS (EI) m/z 333.10 (M−H)⁻.

Example 26

Synthesis of 5-(4-fluoro-phenylcarbamoyl)-pyridin-2-ylsulfanyl]-acetic acid 3-fluoro-benzyl ester

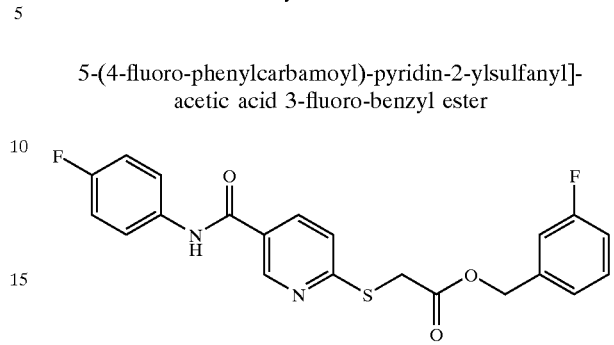

A solution of [5-(4-fluoro-phenylcarbamoyl)-pyridin-2-ylsulfanyl]-acetic acid (0.030 g, 0.10 mmole), 3-fluorobenzyl alcohol (0.10 mL, 1.0 mmol), and sulfuric acid (1 drop) in toluene (5 mL) was heated at reflux. After 2 h the reaction mixture was poured into ethyl acetate and washed with saturated sodium bicarbonate and dried over sodium sulfate. Removal of the solvents provided a solid. Purification by trituration using ethyl acetate/hexanes gave 0.011 g (27%) of the titled product as a white solid: $^1$H NMR (300 MHz, DMSO-d$_6$) δ 10.36 (s 1H); 8.86 (m, 1H); 8.12 (m, 1H); 7.74 (m, 2H); 7.51 (m, 1H); 7.35 (m, 1H); 7.15 (m, 5H); 5.16 (m, 2H), 4.18 (m, 2H); MS (EI) m/z 413.05 (M−H)⁻.

Example 27

Synthesis of

[5-(4-fluoro-phenylcarbamoyl)-pyridin-2-yloxy]-acetic acid tert-butyl ester

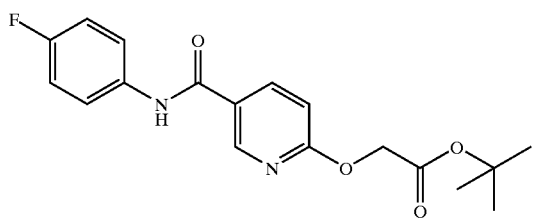

A suspension of 6-bromo-N-(4-fluoro-phenyl)-nicotinamide (0.112 g, 0.38 mmol), tert-butyl glycolate (0.1 g, 0.76 mmol), and potassium tert-butoxide (0.85 g, 0.76 mmol) in THF (10 mL) was heated in a sealed tube at 70° C. After 6 h the reaction mixture was diluted with ethyl acetate and washed with water bicarbonate and dried over sodium sulfate. Removal of the solvents provided a solid. Purification by reverse phase chromatography gave 0.010 g (8%) of the titled product as a white solid; MS (EI) m/z 345.21 (M−H)⁻.

Example 28

Synthesis of

3-[5-(4-fluoro-phenylcarbamoyl)-pyridin-2-ylsulfanyl]-propionic acid

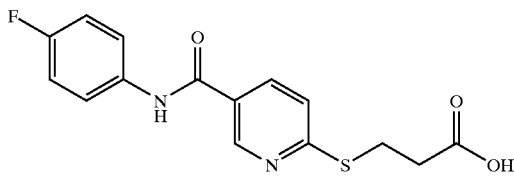

To a solution of 6-chloro-N-(4-fluoro-phenyl)-nicotinamide (0.20 g, 0.80 mmol) in 10 mL of DMF was added 3-mercaptopropionic acid (0.10 mL, 1.2 mmol) and potassium tert-butoxide (0.31 g, 2.8 mmol) and the mixture heated to 60° C. After 9 h the reaction mixture was poured into ice water, HCl (1 M, aq) added to adjust to pH 6, and the solids removed via filtration. The filtrate was then taken to pH 10 with NaOH (4M, aq) and extracted with ethyl acetate. HCl (6M, aq) was then added to the filtrate to adjust the pH to 4 and extracted with ethyl acetate, dried over sodium sulfate, and the solvents removed in vacuo to yield a white solid. Purification by recrystallization using ethyl acetate gave 0.17 g (66%) of the titled product as a white solid; MS (EI) m/z 319.20 (M–H)⁻.

Example 29

Synthesis of

4-[5-(4-Fluoro-phenylcarbamoyl)-pyridin-2-ylsulfanyl]-butyric acid

The titled compound was made in an analogous manner to the preparation of 3-[5-(4-fluoro-phenylcarbamoyl)-pyridin-2-ylsulfanyl]-propionic acid as described in Example 28, where characterization of this product was as follows: MS (EI) m/z 333.22 (M–H)⁻.

Example 30

Synthesis of (5-nitro-pyridin-2-yloxy)-acetic acid methyl ester

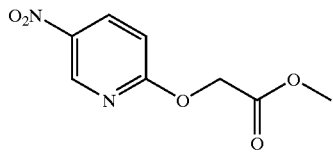

To a solution of 2-chloro-5-nitropyridine (1.0 g, 6.3 mmol) and methyl glycolate (0.67 mL, 8.2 mmol) in THF (10 mL) was added potassium tert-butoxide (0.92 g, 8.2 mmol) in one portion. After 1 h the reaction was poured onto ice, the solids isolated by filtration and washed with water. Purification on silica gel by column chromatography using 20% ethyl acetate in hexanes gave 0.23 g (18%) of the titled product as a white solid: $^1$H NMR (300 MHz, DMSO-$d_6$) δ 9.02 (m, 1H), 7.15 (m, 1H), 5.06 (s, 2H), 3.65 (s, 3H).

Example 31

Synthesis of

[5-(4-fluoro-benzoylamino)-pyridin-2-yloxy]-acetic acid methyl ester

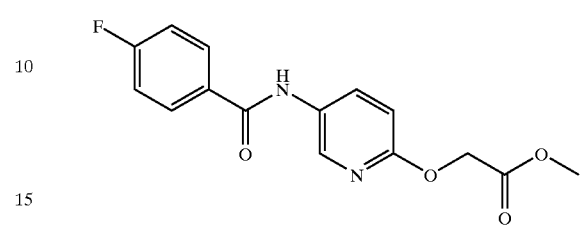

A. To a solution of (5-nitro-pyridin-2-yloxy)-acetic acid methyl ester (0.23 g, 1.08 mmol) in methanol (30 mL) was added palladium on activated carbon (10 wt. %, 0.20 g) and the solution was blanketed with hydrogen at atmospheric pressure. After 4 h the solids were removed by filtration and the volatiles were removed to yield 0.16 g (82%) of (5-amino-pyridin-2-yloxy)-acetic acid methyl ester as an oil that was used without further purification.

B. To a solution of (5-amino-pyridin-2-yloxy)-acetic acid methyl ester (0.16 g, 0.88 mmol) in dichloromethane (5 mL) was added 4-fluorobenzoyl chloride (0.11 mL, 0.97 mmol) and N,N-diisopropylethylamine (0.33 mL, 1.9 mmol). After 24 h the reaction was poured into ethyl acetate, washed with water, and dried over sodium sulfate. Removal of the solvent gave a white solid that was purified by trituration using ethyl acetate/hexanes to give the titled product 0.18 g (67%) as a white solid: $^1$H NMR (300 MHz, DMSO-$d_6$) δ 10.30 (s,1H); 8.40 (m, 1H); 8.03 (m, 3H); 7.35 (m, 2H); 6.92 (m, 1H); 4.87 (m, 2H); 3.64 (m, 3H).

Example 32

Synthesis of

[5-(4-azido-2-hydroxy-benzoylamino)-pyridin-2-yloxy]-acetic acid methyl ester

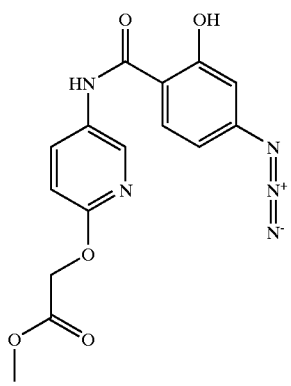

To a mixture of (5-amino-pyridin-2-yloxy)-acetic acid methyl ester (40 mg, 0.19 mmol) and 4-azido-2-hydroxy-benzoic acid 2,5-dioxo-pyrrolidin-1-yl ester (50 mg, 0.192 mmol) in DCM (5 mL) was added DIPEA (66 μL, 0.38 mmol). The mixture was stirred for 15 h at an ambient temperature and was poured into water. The aqueous mixture was extracted with ethyl acetate (3×25 mL) and the combined extracts were washed with brine and dried over magnesium sulfate. Filtration and concentration gave a solid residue that was suspended in a small amount of ethyl acetate (3 mL) and was collected by filtration. This afforded 35.6 mg (54%) of (5-(4-azido-2-hydroxy-benzoylamino)-pyridin-2-yloxy)-acetic acid methyl ester: $^1$H NMR (300 MHz, acetone-$d_6$) δ 11.78 (bs, 1H), 9.89 (s,1H), 7.90 (m, 1H), 7.54 (m, 2H), 6.51 (m, 1H), 6.27 (m, 1H), 6.20 (m, 1H), 4.44 (s, 2H) 3.19 (s, 3H); MS (EI) m/z 341.99 (M–H)$^-$.

Example 33

Synthesis of

[5-(4-azido-2-hydroxy-5-iodo-benzoylamino)-pyridin-2-yloxy]-acetic acid methyl ester

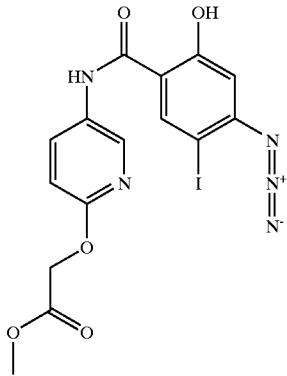

To a suspension of (5-(4-azido-2-hydroxy-benzoylamino)-pyridin-2-yloxy-acetic acid methyl ester (22 mg, 64 mmol) in DMF (1 mL) was added sodium iodide (11 mg, 0.07 mmol) and chloramine T (51 mg, 0.22 mol). The reaction mixture turned homogeneous and after 10 minutes, the mixture was poured into water and was extracted with ethyl acetate (3×25 mL). The combined extracts were washed with water and brine and dried over magnesium sulfate. Filtration and concentration in vacuo gave a residue that was purified via radial chromatography (1 mm plate, 10% ethyl acetate/hexanes as eluant).

This gave 7.8 mg (26%) of (5-(4-azido-2-hydroxy-5-iodo-benzoylamino)-pyridin-2-yloxy)-acetic acid methyl ester as an off-white solid: $^1$H NMR (300 MHz, acetone-$d_6$) δ 9.92 (bs, 1H) 8.40 (m, 1H), 8.33 (s, 1H), 8.05 (m, 1H), 6.92 (m, 1H), 6.87 (s, 1H), 4.90 (s, 2H), 3.69 (s, 3H); MS (EI) m/z 467.97 (M–H)$^-$.

Example 34

Synthesis of

[5-(4-benzoyl-benzoylamino)-pyridin-2-yloxy]-acetic acid methyl ester

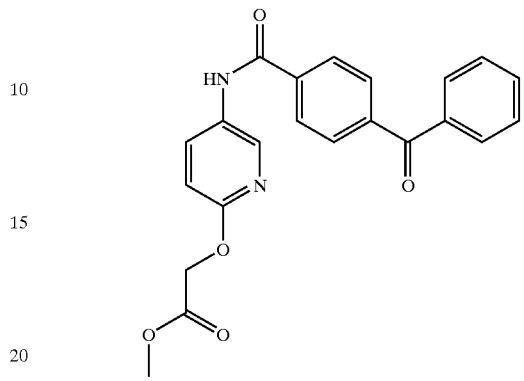

To a mixture of (5-amino-pyridin-2-yloxy)-acetic acid methyl ester (62 mg, 0.31 mmol) 1-(2-(4-benzoyl-phenyl)-2-oxo-ethyl)-pyrrolidine-2,5-dione (100 mg, 0.31 mmol) in DCM (5 mL) was added DIPEA (108 μL, 0.62 mmol) stirring for 4 days, the mixture was poured into ethyl acetate and was washed with brine and dried over magnesium sulfate. Filtration and concentration in vacuo afford a residue that was taken up in DCM (10 mL) and treated with saturated aqueous ammonium hydroxide (1 mL). After 1 h, the mixture was diluted with DCM, washed with water and brine, and dried over magnesium sulfate. Filtration and concentration in vacuo afforded a residue that was purified via radial chromatography (1 mm plate, 10% ethyl acetate/hexanes to 33% ethyl acetate/hexanes as eluants). This afforded 6.8 mg (6%) of (5-(4-benzoyl-benzoylamino)-pyridin-2-yloxy)-acetic acid methyl ester as an off-white solid: $^1$H NMR (300 MHz, acetone-$d_6$) δ 9.8 (bs, 1H), 8.53 (m, 1H) 8.17 (m, 3H), 7.88 (m, 2H), 7.81 (m, 2H), 7.68 (m, 1H), 7.57 (m, 2H), 6.95 (m, 1H), 4.90 (s, 2H), 3.69 (s, 3H); MS (EI) m/z 388.91 (M–H)$^-$.

Example 35

Synthesis of

[5-(4-azido-benzoylamino)-pyridin-2-yloxy]-acetic acid methyl ester

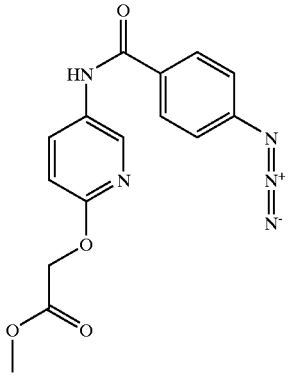

To a mixture of 4-azido-benzoic acid (200 mg, 1.23 mmol) and oxalyl chloride (5 mL) was added a catalytic quantity of DMF (50 μL). The reaction mixture was stirred for 20 minutes and was concentrated in vacuo. Benzene (20 mL) was added and the mixture was again concentrated in vacuo. The resulting residue was dissolved in DCM (5 mL) and was treated with (5-amino-pyridin-2-yloxy)-acetic acid methyl ester (242 mg, 1.33 mmol) followed by DIPEA (427 μL, 2.46 mmol). The reaction mixture was stirred for 15 h at ambient temperature before being diluted with DCM, washed with water and brine and dried over magnesium sulfate. Filtration and concentration in vacuo gave a residue that was taken up in a small portion of ethyl acetate (5 mL) and was precipitated through the addition of hexanes (50 mL). The solids were collected by vacuum filtration on a fritted glass funnel to afford 164 mg (41%) of (5-(4-azido-benzoylamino)-pyridin-2-yloxy)-acetic acid methyl ester as a solid: $^1$H NMR (300 MHz, DMSO-$d_6$) δ 10.25 (bs,1H), 8.39 (m, 1H), 8.00 (m, 3H), 7.24 (m, 2H), 6.92 (m, 1H), 4.87 (s, 2H), 3.63 (s, 3H); MS (EI) m/z326.12 (M–H)$^-$.

Biological Activities of Representative Nicotinamides

GRO-α chemokine inhibitory effects of compounds of the present invention were determined by the following in vitro assays:

Preparation of PMNs

Peripheral blood from healthy human volunteers was collected into heparin, diluted in an equal volume of PBS, layered over Ficoll-Paque Plus (Pharmacia Biotech, Uppsala, Sweden), and spun at 400×g for 30 minutes. The PMN rich fraction was removed and residual erythrocytes were lysed with hypotonic saline. The polymorphonuclear neutrophils (PMNs) were washed once with assay buffer (Dulbecco's PBS containing divalent cations and 0.1% endotoxin-free BSA), and resuspended at 1 E7 cells/mL in the same buffer. PMNs were loaded with 5 μM calcein AM (Molecular Probes, Eugene, Oreg.), washed twice and resuspended in assay buffer.

Chemotaxis Assay

Chemotaxis assays with test compounds of the present invention were generally performed according to the method described by Frevert et al., *J. Immunol. Meth.* 213:41–52 (1998) using either GRO-α or IL-8 as summarized below.

Growth Regulatory Oncogene a (GRO-α) driven chemotaxis assays were performed according to the following protocol. The lower chambers of a ChemoTx plate (Neuro Probe, Gaithersburg, Md.) were filled with 29 μL of 50 nM GRO-α (PeproTech, Rocky Hill, N.J.) and test compound.

The empty upper chambers were affixed to the lower (plate), and 25 μL of PMN suspension (3E6 cells/mL, without (control) or with 0.04–40 μM test compound, pre-incubated 30 minutes, was added to the upper wells. Test compounds were dissolved in DMSO (100%) at 20 mM and diluted in assay buffer to the desired concentrations; final DMSO concentration was 0.2%. Neutrophil migration proceeded for 40 minutes at 37° C. in a humidified incubator with 5% $CO_2$. After removing nonmigrated cells from the top of the plate, migrated cells were quantified by reading fluorescence on a Wallac Victor.

Maximum chemotactic response was determined by cells to which no compound was added (positive control), whereas the negative control (unstimulated) was defined by the absence of chemokine in the lower chamber. The ratio of the positive to negative controls represents the chemotactic index of the cells. The results from this assay are reported in Tables X, under the column heading GRO-α, and under the sub-column headings ChTx (for chemotaxis).

Data obtained by the above-described assays are reported in Tables 1–3. Chemotaxis (%) results are reported as "*" for % values of less than or equal to 40, and "**" for % values greater than 40. When no value appears in a cell, the relevant test was not performed.

The compounds referred to in Table 1 have the following basic structure, and vary only in the identity of R.

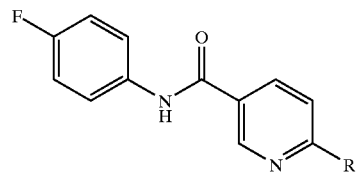

The compounds referred to in Table 2 have the following basic structure, and vary only in the identity of R.

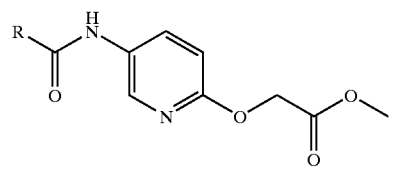

The compounds referred to in Table 3 have the following basic structure, and vary only in the identity of R.

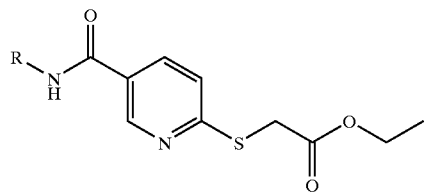

TABLE 1

| R | GRO-α Chemotaxis @ 20 uM, % |
|---|---|
| (S-linked propyl ester group) | ** |
| (S-linked ester group) | ** |
| (S-linked propanoate group) | ** |

TABLE 1-continued
| R | GRO-α Chemotaxis @ 20 uM, % |
|---|---|
| 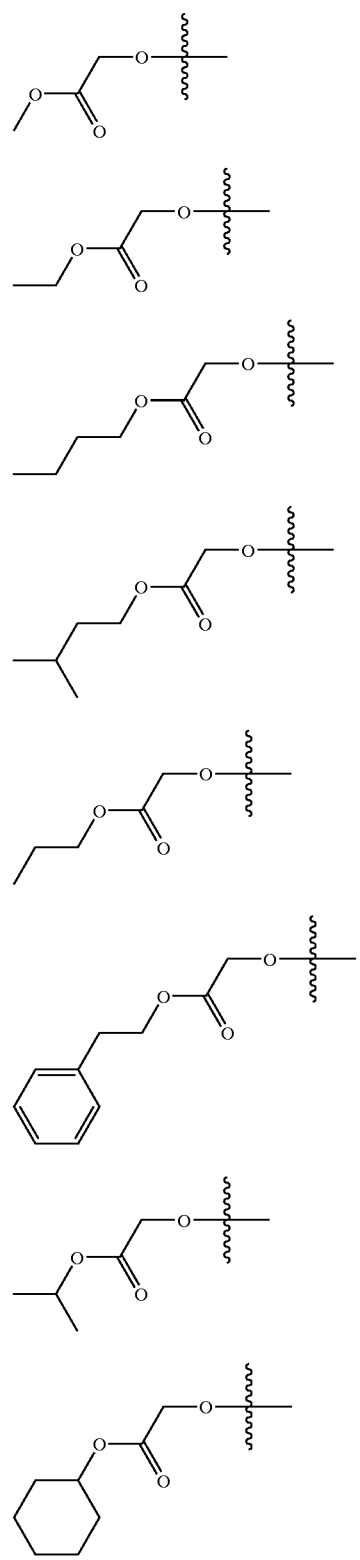 | ** |
| | ** |
| | ** |
| | ** |
| | ** |
| | ** |
| | ** |
| | ** |
TABLE 1-continued
| R | GRO-α Chemotaxis @ 20 uM, % |
|---|---|
| 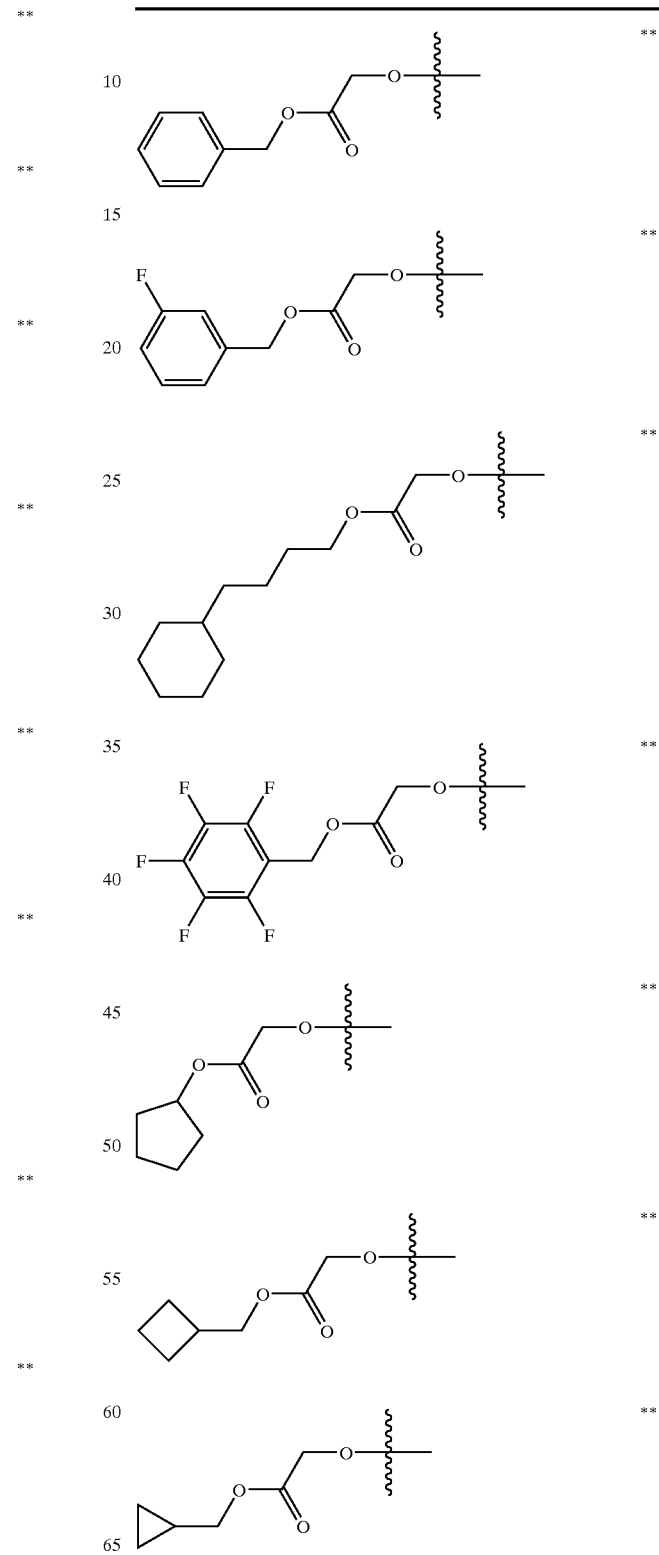 | ** |
| | ** |
| | ** |
| | ** |
| | ** |
| | ** |
| | ** |

TABLE 1-continued
| R | GRO-α Chemotaxis @ 20 uM, % |
|---|---|
| 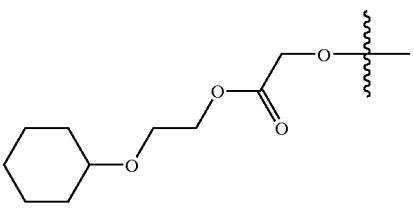 | ** |
| 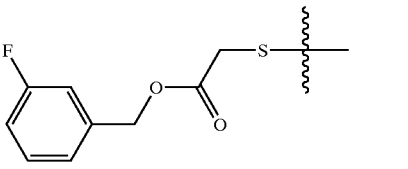 | ** |
| 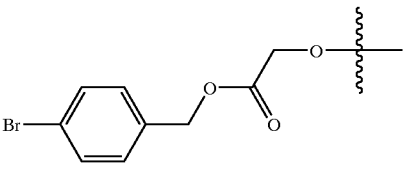 | ** |
| 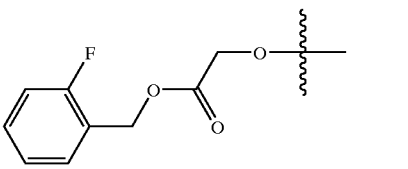 | ** |
| 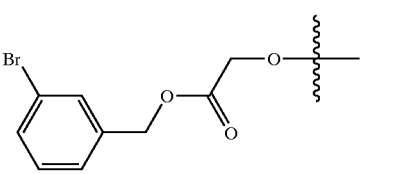 | ** |
| 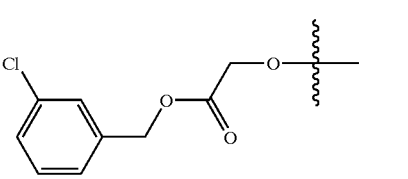 | ** |
| 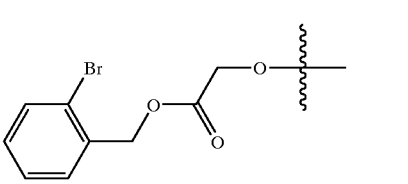 | ** |
| 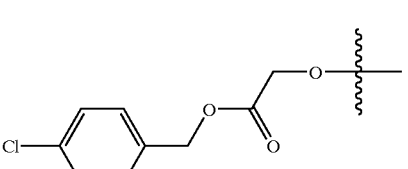 | ** |
TABLE 1-continued
| R | GRO-α Chemotaxis @ 20 uM, % |
|---|---|
| 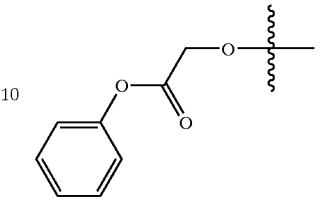 | ** |
| 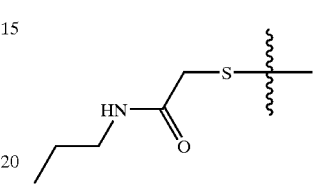 | * |
| 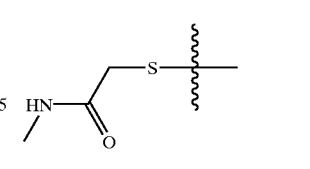 | * |
| 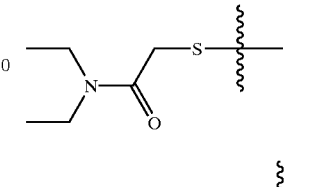 | * |
| 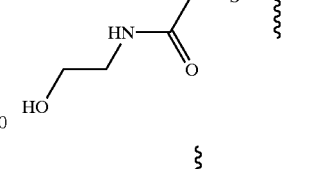 | * |
| 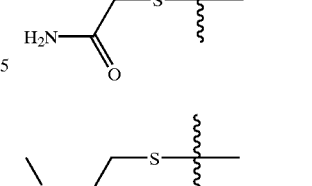 | ** |
| 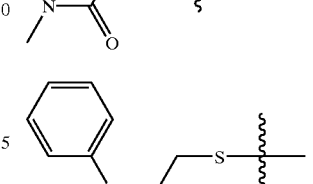 | ** |
| 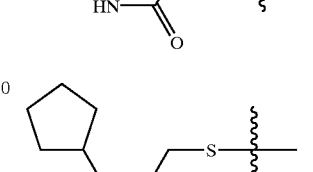 | ** |
|  | ** |

TABLE 1-continued

| R | GRO-α Chemotaxis @ 20 uM, % |
|---|---|
| 4-fluorophenyl-NH-C(O)-CH2-S- | ** |
| N-methyl-N-phenyl-NH-C(O)-CH2-S- | ** |
| pyridin-3-yl-NH-C(O)-CH2-S- | ** |
| 3-bromophenyl-NH-C(O)-CH2-S- | ** |
| tert-butyl-O-C(O)-CH2-O- | ** |
| NaO-C(O)-CH2-S-CH3 | ** |
| HO-C(O)-CH2-S- | ** |
| HO-C(O)-CH2-O- | * |
| HO-C(O)-CH2-CH2-S- | * |
| HO-C(O)-CH2-CH2-CH2-S- | ** |

TABLE 2

| R | GRO-α Chemotaxis @ 20 uM, % |
|---|---|
| 4-fluorophenyl | ** |
| 4-azidophenyl | ** |
| 2-hydroxy-4-azidophenyl | ** |
| 2-hydroxy-4-azido-5-iodophenyl | ** |
| 4-benzoylphenyl | ** |

TABLE 3

| R | GRO-α Chemotaxis @ 20 uM, % |
|---|---|
| ![o-N3 phenyl] | ** |
| ![2-diazo-4-F phenyl] | ** |
| ![3-diazo phenyl] | ** |
| ![3-diazo-4-F phenyl] | ** |
| ![4-diazo phenyl] | ** |
| ![4-I phenyl] | ** |
| ![3-I phenyl] | ** |
| ![3-I-4-methyl phenyl] | ** |
| ![o-NHBoc phenyl] | ** |

Each publication and reference that is set forth herein is hereby incorporated by reference in its entirety for all purposes.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

What is claimed is:

1. A compound of the formula

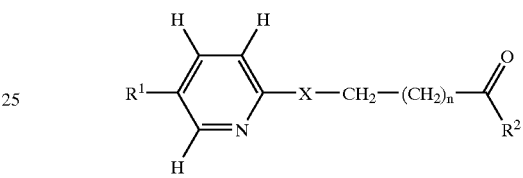

and prodrugs, solvates and pharmaceutically acceptable salts thereof, wherein $R^1$ is selected from

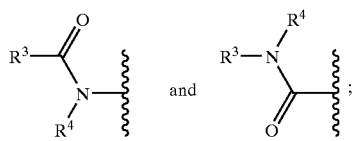

$R^2$ is selected from

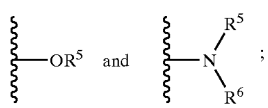

n is 0, 1, 2 or 3;

X is selected from oxygen and sulfur; and $R^3$, $R^4$, $R^5$ and $R^6$ are independently selected from hydrogen, alkyl, heteroalkyl, aryl, aryl(akylene), heteroaryl, heteroaryl(alkylene), carbocycle, carbocycle(alkylene), heterocycle, and heterocycle (alkylene).

2. A compound of claim 1 wherein $R^1$ is

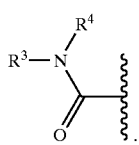

3. A compound of claim 2 wherein $R^2$ is

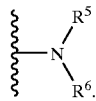

4. A compound of claim 2 wherein $R^2$ is

5. A compound of claim 2 wherein X is oxygen.
6. A compound of claim 2 wherein X is sulfur.
7. A compound of claim 2 wherein n is 0.
8. A compound of claim 1 wherein $R^1$ is

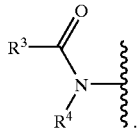

9. A compound of claim 8 wherein $R^2$ is

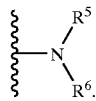

10. A compound of claim 8 wherein $R^2$ is

11. A compound of claim 8 wherein X is oxygen.
12. A compound of claim 8 wherein X is sulfur.
13. A compound of claim 8 wherein n is 0.
14. A compound of claim 2 wherein $R^3$ is hydrogen or lower alkyl; $R^4$ is aryl; n is 0 or 1; $R^2$ is $-OR^5$; and $R^5$ is selected from hydrogen and $C_1-C_{10}$alkyl, $C_1-C_{10}$heteroalkyl, $C_6-C_{12}$aryl, $C_6-C_{12}$aryl($C_1-C_6$akylene), $C_1-C_6$heteroaryl, $C_1-C_6$heteroaryl($C_1-C_6$alkylene), $C_5-C_{10}$carbocycle, $C_5-C_{10}$-carbocycle($C_1-C_6$alkylene), $C_1-C_6$heterocycle, and $C_1-C_6$heterocycle($C_1-C_6$alkylene).
15. A compound of claim 14 wherein $R^5$ is selected from hydrogen and $C_1-C_{10}$alkyl, $C_6-C_{12}$aryl, $C_6-C_{12}$aryl($C_1-C_6$alkylene), $C_5-C_{10}$carbocycle, and $C_5-C_{10}$carbocycle($C_1-C_6$alkylene).
16. A compound of claim 2 wherein n is 0; $R^3$ is hydrogen and $R^4$ is phenyl substituted with one or more groups selected from fluorine, azide, hydoxyl, iodide and methyl.
17. A compound of claim 2 wherein n is 0, and $R^2$ is

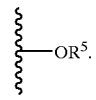

18. A compound of claim 17 wherein $R^3$ is hydrogen, $R^4$ is phenyl, and $R^5$ is hydrogen or alkyl.
19. A compound of claim 17 selected from:

[5-(4-fluoro-phenylcarbamoyl)-pyridin-2-ylsulfanyl]-acetic acid methyl ester;

[5-(4-fluoro-phenylcarbamoyl)-pyridin-2-yloxy]-acetic acid methyl ester;

[5-(4-fluoro-phenylcarbamoyl)-pyridin-2-yloxy]-acetic acid butyl ester;

5-(4-fluoro-phenylcarbamoyl)-pyridin-2-ylsulfanyl]-acetic acid; and

[5-(4-fluoro-phenylcarbamoyl)-pyridin-2-yloxy]-acetic acid;

and pharmaceutically acceptable salts thereof.

20. A compound of claim 2 wherein n is 0, and $R^2$ is

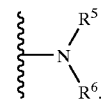

21. A compound of claim 20 wherein $R^3$ is hydrogen, $R^4$ is phenyl, $R^5$ is alkyl, aryl or heteroaryl, and $R^6$ is hydrogen or alkyl.
22. A compound of claim 20 which is:

N-(4-fluoro-phenyl)-6-(pyridin-3-ylcarbamoylmethylsulfanyl)-nicotinamide;

and pharmaceutically acceptable salts thereof.

23. A compound of claim 8 wherein $R^3$ is aryl; n is 0 or 1; $R^2$ is $-OR^5$; and $R^5$ is selected from hydrogen and $C_1-C_{10}$alkyl, $C_1-C_{10}$heteroalkyl, $C_6-C_{12}$aryl, $C_6-C_{12}$aryl($C_1-C_6$akylene), $C_1-C_6$heteroaryl, $C_1-C_6$heteroaryl($C_1-C_6$alkylene), $C_5-C_{10}$ carbocycle, $C_5-C_{10}$carbocycle($C_1-C_6$alkylene), $C_1-C_6$heterocycle, and $C_1-C_6$heterocycle($C_1-C_6$alkylene), and $R^4$ is hydrogen or lower alkyl.
24. A compound of claim 8 wherein $R^3$ is aryl; n is 0 or 1; $R^2$ is $-OR^5$; and $R^5$ is selected from hydrogen and $C_1-C_{10}$alkyl, $C_6-C_{12}$aryl, $C_6-C_{12}$aryl($C_1-C_6$akylene), $C_1-C_6$heteroaryl, and $C_1-C_6$heteroaryl($C_1-C_6$alkylene), and $R^4$ is hydrogen or lower alkyl.
25. A compound of claim 8 wherein n is 0; $R^3$ is phenyl substituted with one or more groups selected from fluorine, azide, hydroxyl, iodide and methyl, and $R^4$ is hydrogen.
26. A compound of claim 8 wherein n is 0, and $R^2$ is

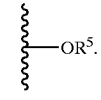

27. A compound of claim 26 wherein $R^3$ is phenyl, $R^4$ is hydrogen, and $R^5$ is hydrogen or alkyl.
28. A compound of claim 26 that is:

[5-(4-fluoro-benzoylamino)-pyridin-2-yloxy]-acetic acid methyl ester, and pharmaceutically acceptable salts thereof.

29. A compound of claim 8 wherein n is 0, and $R^2$ is

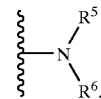

30. A compound of claim 29 wherein $R^3$ is phenyl, $R^4$ is hydrogen, $R^5$ is alkyl, aryl or heteroaryl, and $R^6$ is hydrogen or alkyl.

31. A compound of the formula

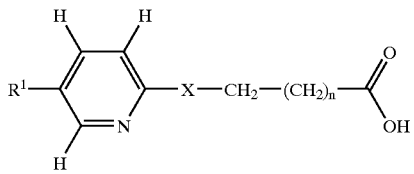

and prodrugs, solvates, and pharmaceutically acceptable salts thereof, wherein $R^1$ is selected from

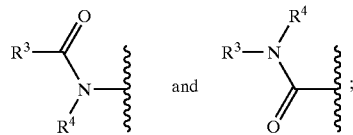

n is 0, 1, 2 or 3;

X is selected from oxygen and sulfur; and $R^3$, $R^4$, $R^5$ and $R^6$ are independently selected from hydrogen, alkyl, heteroalkyl, aryl, aryl(akylene), heteroaryl, heteroaryl(alkylene), carbocycle, carbocycle(alkylene), heterocycle, and heterocycle(alkylene).

32. A compound of claim 31 wherein $R^1$ is

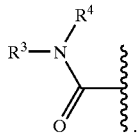

33. A compound of claim 32 wherein X is oxygen.
34. A compound of claim 32 wherein X is sulfur.
35. A compound of claim 32 wherein n is 0.

36. A compound of claim 31 wherein $R^1$ is

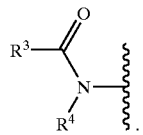

37. A compound of claim 36 wherein X is oxygen.
38. A compound of claim 36 wherein X is sulfur.
39. A compound of claim 36 wherein n is 0.
40. A compound of claims 31–39 wherein $R^3$ is aryl; $R^4$ is hydrogen or lower alkyl; and n is 0 or 1.
41. A compound of claim 31 wherein n is 0; $R^3$ is phenyl substituted with one or more groups selected from fluorine, azide, hydoxyl, iodide and methyl; and $R^4$ is hydrogen.
42. A compound of claim 31 wherein $R^3$ is aryl; n is 0 or 1; and $R^4$ is hydrogen or lower alkyl.
43. A compound of claim 31 wherein $R^3$ is aryl; n is 0 or 1; and $R^4$ is hydrogen or lower alkyl.
44. A compound of claim 31 wherein n is 0; $R^3$ is phenyl substituted with one or more groups selected from fluorine, azide, hydoxyl, iodide and methyl, and $R^4$ is hydrogen.
45. A compound of claim 31, which is a pharmaceutically acceptable salt of the shown compound.
46. A compound of claim 31, which is a prodrug of the shown compound.
47. A compound of claim 46 wherein the prodrug is an ester of the shown compound.
48. A composition comprising a compound of any of claims 1–47 and a pharmaceutically acceptable carrier, excipient or diluent.
49. A method of treating a subject having an inflammatory disorder alleviated by the inhibition of GRO-α, wherein the method comprises administering to the subject in need thereof an effective amount of a compound of any of claims 1–47.
50. A method of claim 49 wherein the inflammatory disorder is selected from the group consisting of sepsis-related acute respiratory distress syndrome, arthritis, gouty synovitis, atherosclerosis, Alzheimer's disease, ulcerative colitis, psoriasis, and tumor growth and metastasis.

* * * * *